United States Patent
Vince et al.

(10) Patent No.: US 11,819,276 B2
(45) Date of Patent: *Nov. 21, 2023

(54) HYPERSPECTRAL IMAGING FOR EARLY DETECTION OF ALZHEIMER'S DISEASE

(71) Applicant: REGENTS OF THE UNIVERSITY OF MINNESOTA, Minneapolis, MN (US)

(72) Inventors: Robert Vince, Minneapolis, MN (US); Swati Sudhakar More, Minneapolis, MN (US)

(73) Assignee: REGENTS OF THE UNIVERSITY OF MINNESOTA, Minneapolis, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 17/939,566

(22) Filed: Sep. 7, 2022

(65) Prior Publication Data

US 2023/0106874 A1 Apr. 6, 2023

Related U.S. Application Data

(63) Continuation of application No. 16/160,208, filed on Oct. 15, 2018, now Pat. No. 11,503,999, which is a
(Continued)

(51) Int. Cl.
*G01J 3/28* (2006.01)
*A61B 3/12* (2006.01)
(Continued)

(52) U.S. Cl.
CPC .............. *A61B 3/12* (2013.01); *A61B 3/14* (2013.01); *A61B 5/4848* (2013.01);
(Continued)

(58) Field of Classification Search
CPC .... A61B 5/00; A61B 3/00; A61B 3/12; A61B 3/14; A61B 5/4848; A61K 38/063;
(Continued)

(56) References Cited

U.S. PATENT DOCUMENTS 6,600,947 B2  7/2003  Averback et al.
6,992,775 B2  1/2006  Soliz et al.
(Continued)

FOREIGN PATENT DOCUMENTS

EP  1913866 A1  4/2008
JP  2017029533 A  2/2017
(Continued)

OTHER PUBLICATIONS

Bons, et al., "BSE infection of the small short-lived primate *Microcebus murinus*", C. R. Biologies 325, 67-74 (2002).
(Continued)

*Primary Examiner* — Abdullahi Nur
(74) *Attorney, Agent, or Firm* — Viksnins Harris Padys Malen LLP

(57) ABSTRACT

Described herein is the use of a visible near infrared (VNIR) hyperspectral imaging system as a non-invasive diagnostic tool for early detection of Alzheimer's disease (AD). Also described herein is the use of a VNIR hyperspectral imaging system in high throughput screening of potential therapeutics against AD.

26 Claims, 14 Drawing Sheets

Related U.S. Application Data continuation of application No. 15/449,585, filed on Mar. 3, 2017, now Pat. No. 10,098,540, which is a continuation of application No. 14/363,953, filed as application No. PCT/US2012/068793 on Dec. 10, 2012, now Pat. No. 9,585,558.

(60) Provisional application No. 61/568,983, filed on Dec. 9, 2011.

(51) Int. Cl.
| | | |
|---|---|---|
| *G01N 21/31* | (2006.01) | |
| *G01J 3/00* | (2006.01) | |
| *G01J 3/40* | (2006.01) | |
| *G01N 21/25* | (2006.01) | |
| *A61B 3/14* | (2006.01) | |
| *A61K 38/06* | (2006.01) | |
| *G01N 33/50* | (2006.01) | |
| *A61B 5/00* | (2006.01) | |

(52) U.S. Cl.
CPC .............. *A61K 38/063* (2013.01); *G01J 3/00* (2013.01); *G01J 3/28* (2013.01); *G01J 3/40* (2013.01); *G01N 21/25* (2013.01); *G01N 21/31* (2013.01); *G01N 33/5038* (2013.01)

(58) Field of Classification Search
CPC ...... G01J 3/00; G01J 3/28; G01J 3/40; G01N 21/25; G01N 21/31; G01N 33/5038
See application file for complete search history.

(56) References Cited

U.S. PATENT DOCUMENTS

| | | | |
|---|---|---|---|
| 7,107,092 | B2 | 9/2006 | Goldstein et al. |
| 7,653,428 | B2 | 1/2010 | Goldstein et al. |
| 7,854,510 | B2 | 12/2010 | Verdooner et al. |
| 8,109,634 | B2 | 2/2012 | Gil et al. |
| 8,237,844 | B2 | 8/2012 | Blais-Ouellette et al. |
| 8,388,134 | B2 | 3/2013 | Goldstein et al. |
| 8,537,260 | B2 | 9/2013 | Daigle |
| 8,814,362 | B2 | 8/2014 | Verdooner |
| 8,955,969 | B2 | 2/2015 | Hartung et al. |
| 9,220,403 | B2 | 12/2015 | Hartung et al. |
| 9,314,155 | B2 | 4/2016 | Verdooner |
| 9,451,909 | B2 | 9/2016 | Hartung et al. |
| 9,521,975 | B2 | 12/2016 | Verdooner et al. |
| 9,566,000 | B2 | 2/2017 | Verdooner et al. |
| 9,585,558 | B2 | 3/2017 | Vince et al. |
| 9,730,580 | B2 | 8/2017 | Verdooner et al. |
| 9,808,155 | B2 | 11/2017 | Verdooner et al. |
| 10,098,540 | B2 | 10/2018 | Vince et al. |
| 11,503,999 | B2 | 11/2022 | Vince et al. |
| 2004/0152068 | A1 | 8/2004 | Goldstein et al. |
| 2007/0002276 | A1 | 1/2007 | Hirohara et al. |
| 2007/0224694 | A1 | 9/2007 | Puchalski |
| 2008/0102487 | A1 | 5/2008 | Yao et al. |
| 2010/0056928 | A1 | 3/2010 | Zuzak et al. |
| 2010/0105098 | A1 | 4/2010 | Frederiske et al. |
| 2010/0110515 | A1 | 5/2010 | Blais-Ouellette et al. |
| 2010/0328661 | A1 | 12/2010 | Blais-Ouellette et al. |
| 2011/0286932 | A1 | 11/2011 | Koronyo et al. |
| 2012/0004856 | A1* | 1/2012 | Matsui ............... A61B 5/0059 702/19 |
| 2012/0101371 | A1 | 4/2012 | Verdooner et al. |
| 2012/0207681 | A1 | 8/2012 | Verdooner |
| 2012/0251452 | A1 | 10/2012 | Verdooner |
| 2012/0327406 | A1 | 12/2012 | Dubowski et al. |
| 2013/0259071 | A1 | 10/2013 | Blais-Ouellette |
| 2014/0154703 | A1 | 6/2014 | Skelley et al. |
| 2014/0176908 | A1 | 6/2014 | Verdooner et al. |
| 2014/0180081 | A1 | 6/2014 | Verdooner et al. |
| 2014/0350379 | A1 | 11/2014 | Verdooner |
| 2016/0206199 | A1 | 7/2016 | Blanco et al. |
| 2016/0278677 | A1 | 9/2016 | Kerbage et al. |
| 2017/0319063 | A1 | 11/2017 | Verdooner et al. |
| 2019/0150733 | A1 | 5/2019 | Vince et al. |
| 2022/0026356 | A1 | 1/2022 | Vince et al. |

FOREIGN PATENT DOCUMENTS

| | | | |
|---|---|---|---|
| WO | 2003018068 | A1 | 3/2003 |
| WO | 2008144065 | A1 | 11/2008 |
| WO | 2010033861 | A1 | 3/2010 |
| WO | 2012045177 | A1 | 4/2012 |
| WO | 2012061078 | A2 | 5/2012 |
| WO | 2012135382 | A1 | 10/2012 |
| WO | 2015066270 | A1 | 5/2015 |
| WO | 2015072964 | A1 | 5/2015 |
| WO | 2016041062 | A1 | 3/2016 |
| WO | 2018026683 | A1 | 2/2018 |

OTHER PUBLICATIONS

Citron, M , "Alzheimer's disease: strategies for disease modification", Nature Reviews 9, 387-398 (2010).
European Patent Office , Communication pursuant to Rule 114(2) EPC for EP Application No. 12856219.6, 4 pages, dated Aug. 6, 2020.
Irvine , et al., "Protein aggregation in the brain: the molecular basis for Alzheimer's and Parkinson's diseases", Molecular Medicine 14, (7-8), 451-464 (2008).
Khoobehi , et al., "Hyperspectral imaging for measurement of oxygen saturation in the optic nerve head", Invest Ophthalmol Vis Sci 45, 1464-1472 (2004).
Koronyo-Hamaoui , et al., "Identification of amyloid plaques in retinas from Alzheimer's patients and noninvasive In vivo optical imaging of retinal plaques in a mouse model", Neuroimage 54 Supp 1, S204-S217 (2011).
KYLE , "Amyloidosis: a convoluted story", British Journal of Haematology 144 (3), 529-538 (2001).
Li, Q , et al., "Quantitative Analysis of Protective Effect of Erythropoietin on Diabetic Retinal Cells Using Molecular lyperspectral Imaging Technology", IEEE Transactions on Biomedical Engineering 57(7), 1699-1706 (2010).
More , et al., "Restoration of glyoxalase enzyme activity precludes cognitive dysfunction in a mouse model of Alzheimer's disease", ACS Chem. Neurosci. 4(2), 330-338 (2013).
Park , et al., "Contaminant Classification of Poultry Hyperspectral Imagery using a Spectral Angle Mapper Algorithm", Biosys Eng. 96 (3), 323-333 (2007).
Patent Cooperation Treaty , International Searching Authority, Search Report and Written Opinion for PCT/US2012/068793, 17 pages, dated Apr. 19, 2013.
Siddiqi , et al., "Use of hyperspectral imaging to distinguish normal, precancerous, and cancerous cells", Cancer vol. 114, 13-21 (2008).
Unknown , "More than just mad cow disease", Nature Structural Biology 8 (4), 281 (2001). [No Author listed].
Vince, et al., "Hyperspectral Imaging Signatures Detect Amyloidopathy in Alzheimer's Mouse Retina Well before Onset of Cognitive Decline", ACS Chem. Neurosci. 6, 306-315 (2015).
Wijngaarden, P , et al., "Emerging ocular biomarkers of Alzheimer disease", Clinical and Experimental Ophthalmology 45(1), 54-61 (2017).

* cited by examiner

HYPERSPECTRAL IMAGING FOR EARLY DETECTION OF ALZHEIMER'S DISEASE

CROSS-REFERENCE TO RELATED APPLICATION(S)

This patent application is a continuation of U.S. application Ser. No. 16/160,208, filed on Oct. 15, 2018, which is a continuation of U.S. application Ser. No. 15/449,585, filed on Mar. 3, 2017, now U.S. Pat. No. 10,098,540, which is a continuation of U.S. application Ser. No. 14/363,953, filed on Jun. 9, 2014, now U.S. Pat. No. 9,585,558, which is a 35 U.S.C. § 371 application of International Application No. PCT/US2012/068793, filed on Dec. 10, 2012, which claims the benefit of priority of U.S. application Ser. No. 61/568,983, filed Dec. 9, 2011, which applications are herein incorporated by reference.

BACKGROUND

There are currently no methods for detecting Alzheimer's Disease (AD) prior to β-amyloid plaque formation. Unfortunately, current methods can detect AD only after a patient starts showing cognitive symptoms. As such, methods to detect AD at an early stage, e.g., before β-amyloid plaque formation, are needed.

Summary of Certain Embodiments of the Invention

Accordingly, certain embodiments of the present invention provide a method for determining whether a subject has Alzheimer's Disease (AD), or is predisposed for developing AD, comprising obtaining a hyperspectral image (HSI) from the eye (e.g., the retina) of the subject and determining whether the HSI comprises spectral differences that are indicative of AD, wherein the presence of said spectral differences that are indicative of AD indicates the subject has, or is predisposed (e.g., at an elevated risk as compared to the general population) for developing, AD. Whether a subject is at an elevated risk as compared to the general population for developing AD is determined by the presence of risk factors detected by HSI, e.g., in the absence of blatant morphological changes in brain or retina tissue of the patient, such as β-amyloid plaque formation.

In certain embodiments, the HSI is a visible near infrared (VNIR) HSI.

In certain embodiments, the HSI is obtained using wavelengths up to about 2500 nm. In certain embodiments, the HSI is obtained using wavelengths from about 400 nm to about 2500 nm, e.g., about 400 nm to about 1400 nm, e.g., about 400 nm to about 1000 nm.

In certain embodiments, the HSI is compared to at least a first previous HSI obtained from the subject at an earlier point in time (e.g., from at least one previous annual check-up), wherein significant spectral differences between the HSI images indicates the subject has AD.

In certain embodiments, the HSI from the subject is compared to a control reference HSI and to an AD reference HSI to determine whether the image comprises spectral differences that are indicative of AD.

In certain embodiments, the subject (e.g., a human male or female) is from about 30-80 years old, e.g., 30-50 years old. In certain embodiments, the subject is about 25-30 years old, about 30-35 years old, about 35-40 years old, about 40-45 years old, about 45-50 years old, about 50-55 years old, or about 55-60 years old.

In certain embodiments, the HSI(s) is/are obtained via a retina examination through whole eye of a patient.

In certain embodiments, the subject is a male.

In certain embodiments, the subject is a female.

Certain embodiments of the present invention provide a method for determining whether a treatment is effective in treating Alzheimer's Disease (AD), comprising determining whether the treatment causes a decrease in spectral differences that are indicative of Alzheimer's Disease (AD) from a hyperspectral image (HSI) from a retina examination, e.g., through the whole eye of a patient. In certain embodiments, the method is an in vitro method.

In certain embodiments, the methods described herein are in vivo methods.

In certain embodiments, the methods described herein are in vitro methods.

In certain embodiments, the sample is retinal tissue.

Certain embodiments of the present invention provide a method for using hyperspectral imaging for determining whether a test compound affects β-amyloid aggregation, comprising contacting a cell that comprises β-amyloid with the test compound, obtaining a hyperspectral image (HSI) of the cell, and determining whether the test compound affects β-amyloid aggregation.

In certain embodiments, a decrease in β-amyloid aggregation indicates that the test compound is an inhibitor of β-amyloid aggregation.

In certain embodiments, the β-amyloid is $A\beta_{1-42}$.

In certain embodiments, the method is an in vitro method.

In certain embodiments, the method is an in vivo method.

In certain embodiments, the cell is comprised in a population of cells in a retina.

In certain embodiments, the HSI is a visible near infrared (VNIR) HSI.

DETAILED DESCRIPTION

Figure 1:
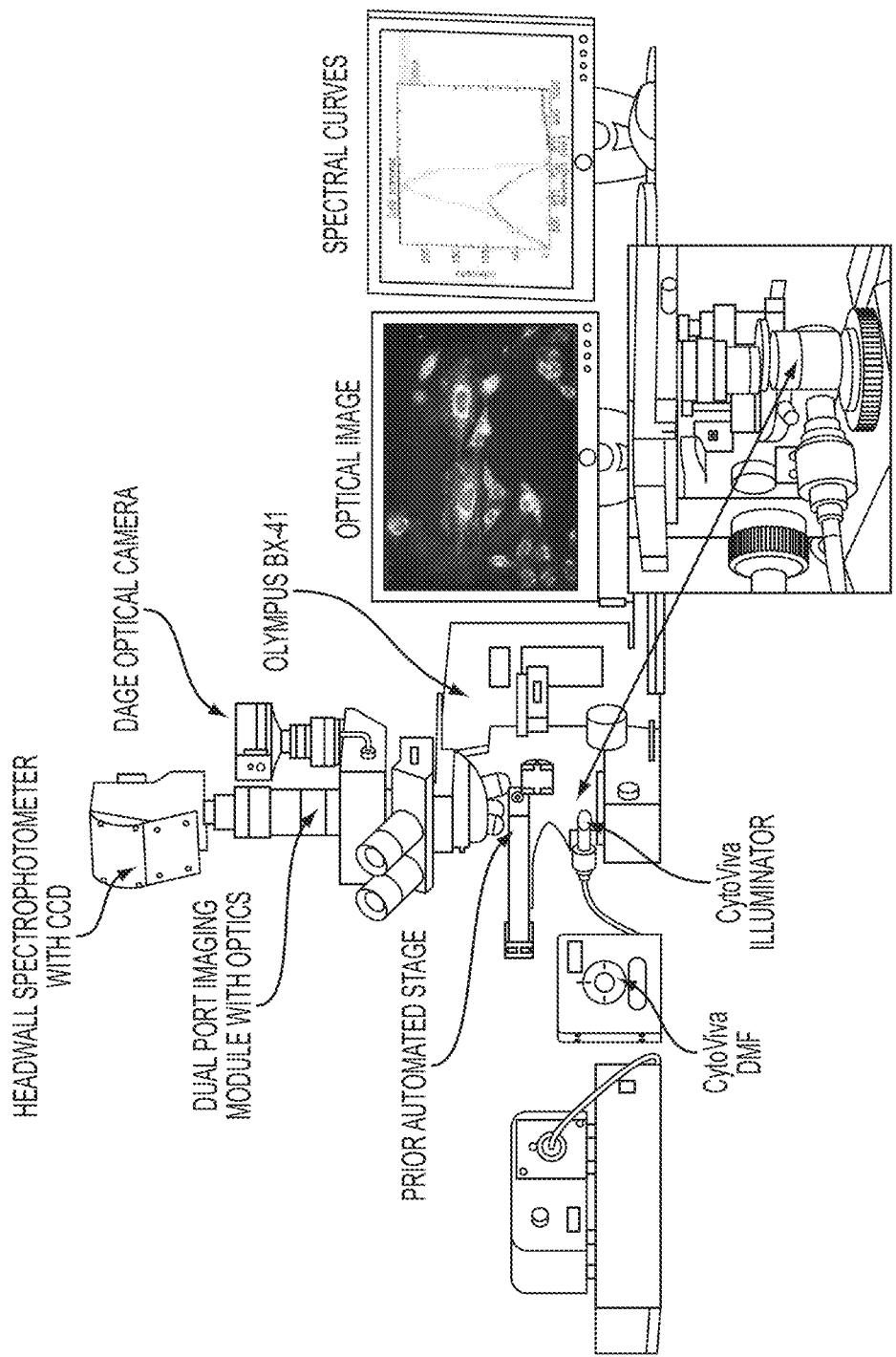
FIG. 1 depicts a VNIR hyperspectral imaging system integrated into a microscope assembly, thereby enabling pixel-level spectral quantification of the sample being imaged. This image shows the assembly with a Cytoviva microscope.
Figure 2:
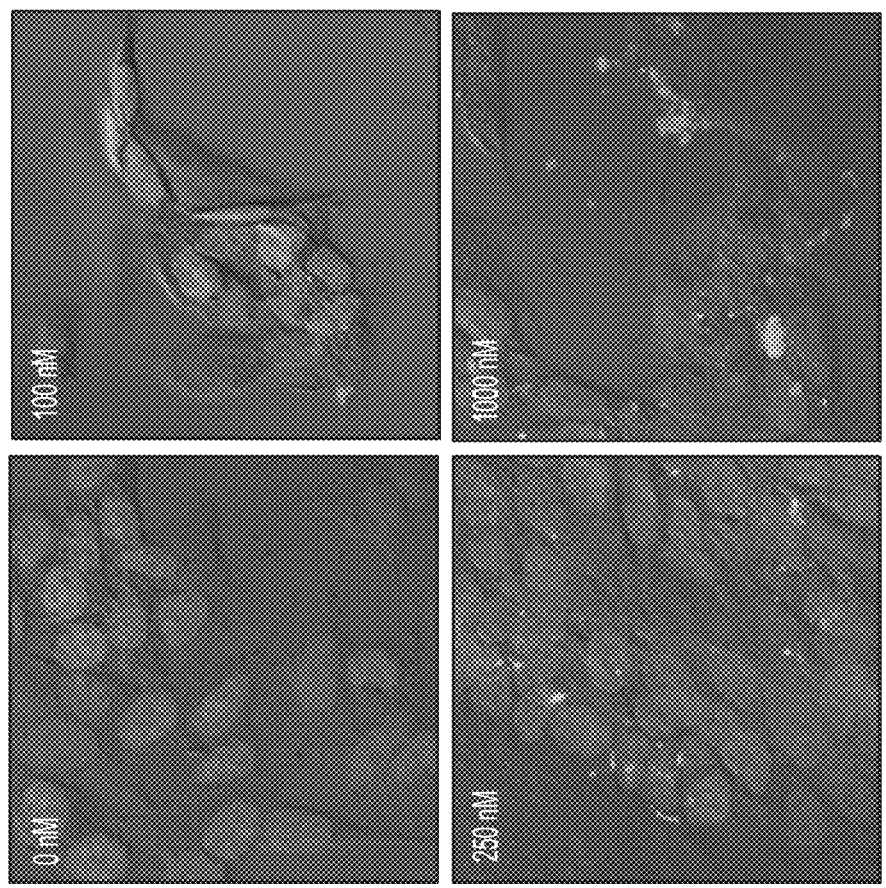
FIG. 2 depicts the concentration-dependent uptake of FITC-labeled β-amyloid peptide. As the concentration of β-amyloid peptide in the extracellular medium was increased, there was a dose-dependent increase in the uptake of β-amyloid peptide inside SH-SY-5Y cells. This is visible as aggregates inside the cells.
Figure 3:
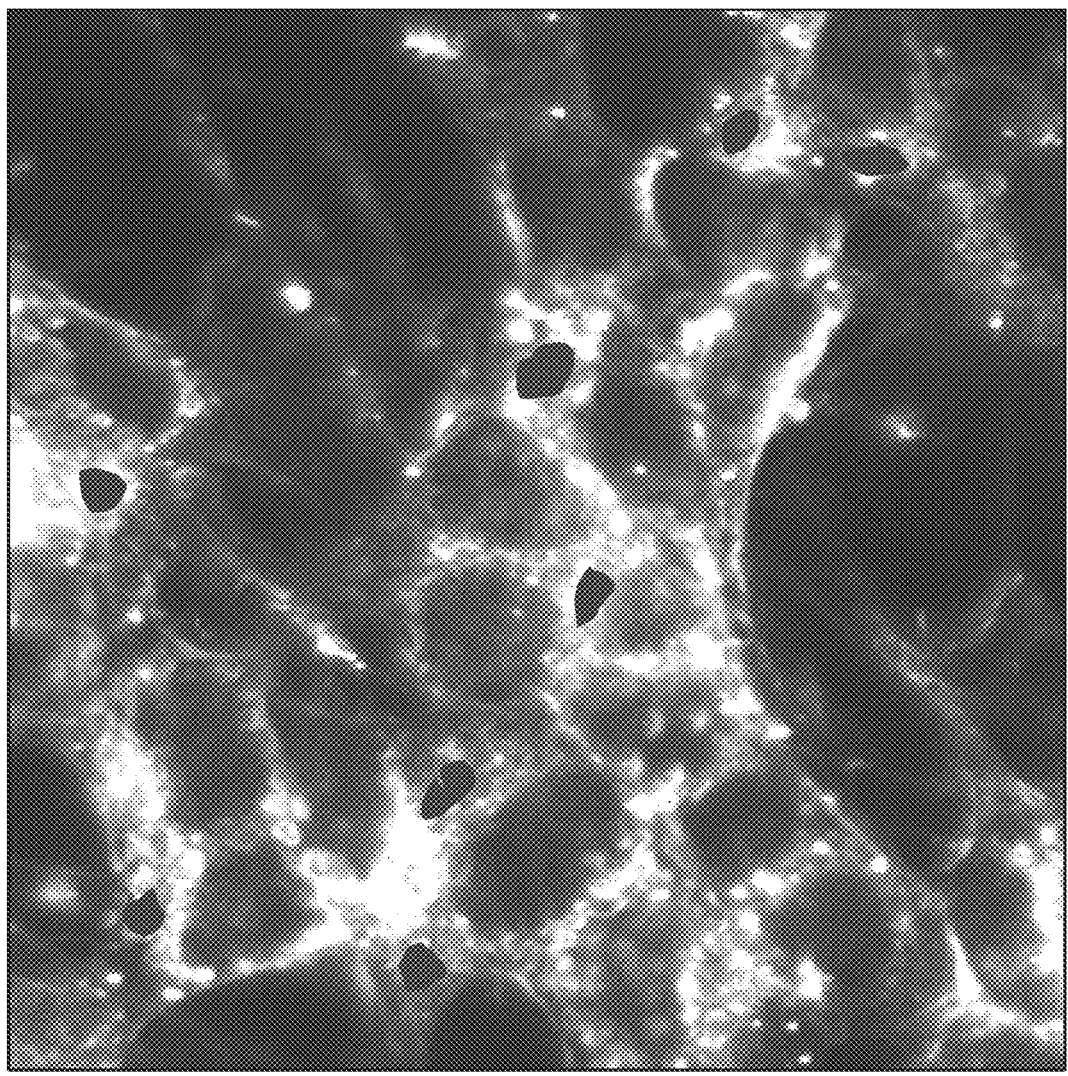
FIG. 3 depicts a typical hyperspectral image from cells. After obtaining the images, several areas in the cytoplasm of cells were selected. These are the areas from which spectra were collected are the ROI (Regions Of Interest), displayed as solid black regions.
Figure 4:
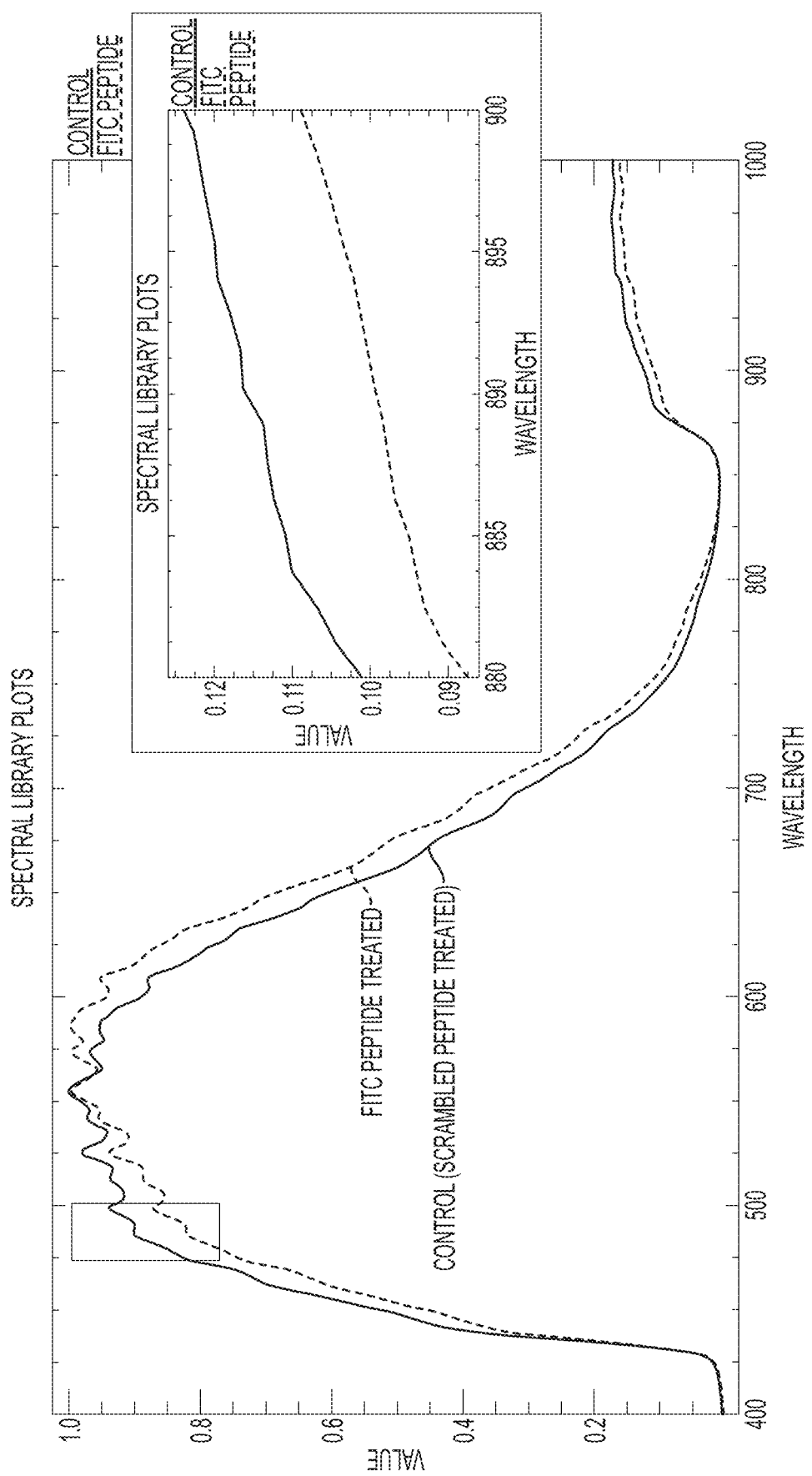
FIG. 4 depicts a graph of the cytoplasm of SH SY5Y cells. Spectral information in the range of 400-1000 nm was extracted from the selected ROIs. This data was then normalized and the means with standard deviation calculated. This figure shows typical data from the cytoplasm of β-amyloid peptide treated and non-treated cells, with focusing on the regions (480-500 nm) and (880-900 nm) where the maximum statistically significant differences were observed.
Figure 5:
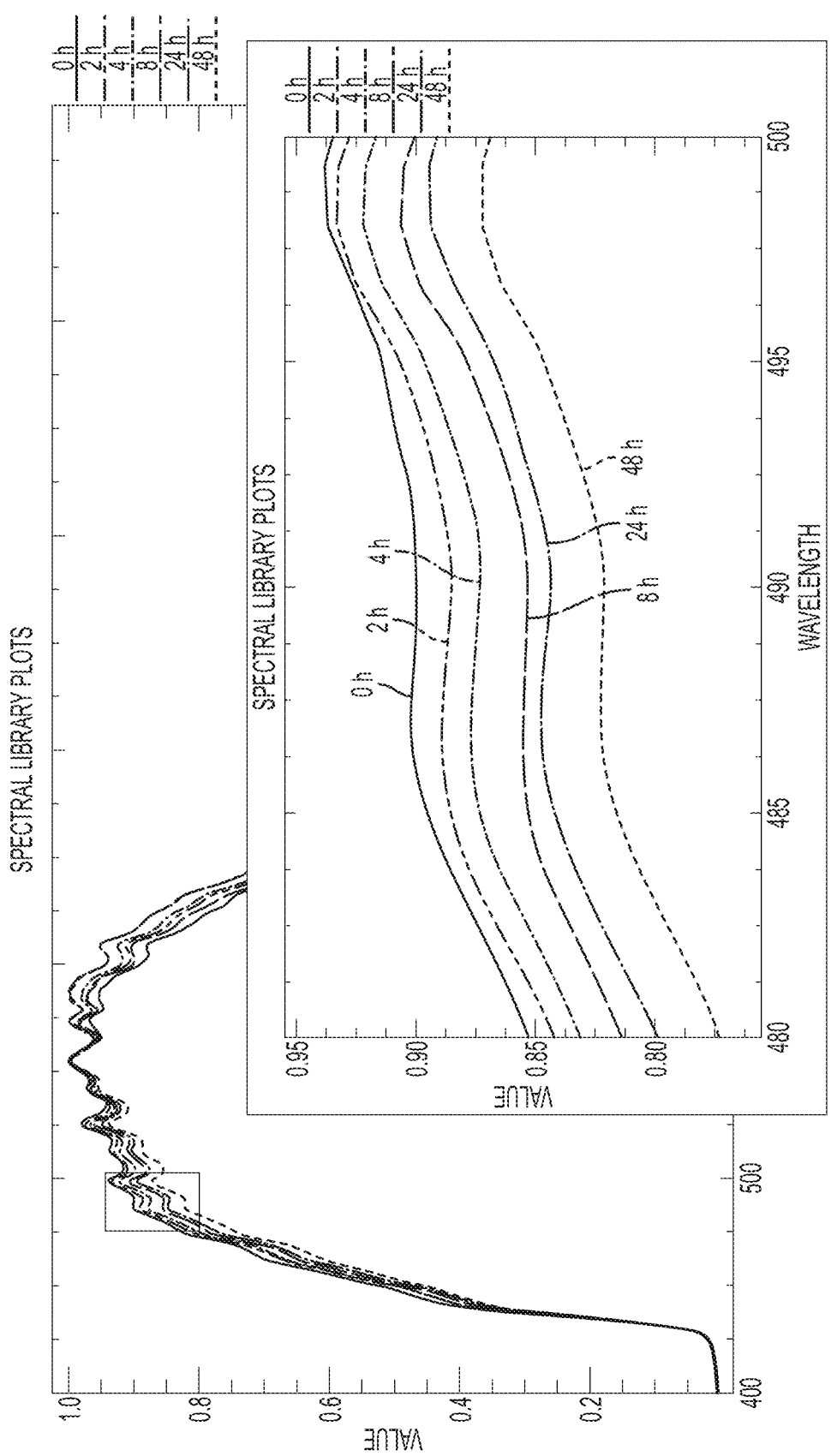
FIG. 5 depicts the time-dependence of cytoplasmic differences between β-amyloid-treated and untreated cells. These data suggest that the spectral changes observed are also time-dependent. The maximal spectral change after β-amyloid peptide treatment was observed after 48 h. However, the spectral data can be analyzed as early as 4 hours, making it attractive from the point of view of high throughput screening.
Figure 6:
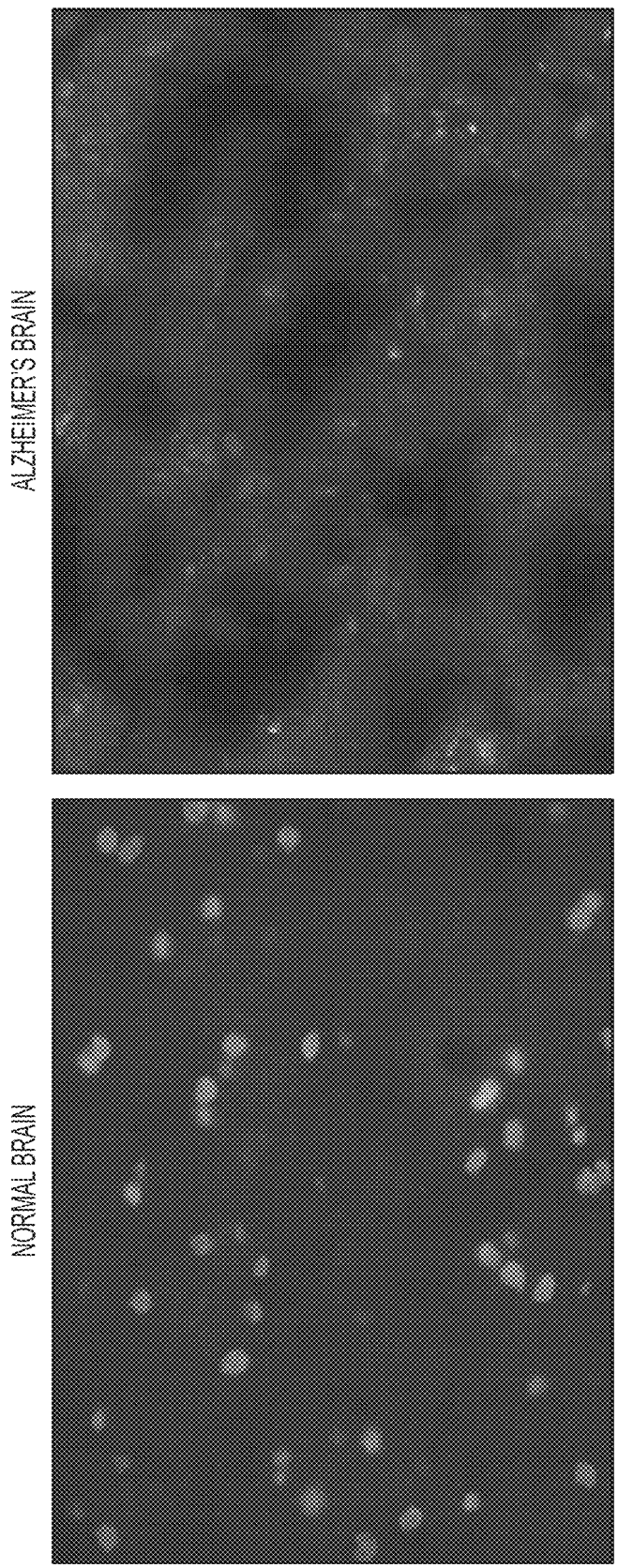
FIG. 6 depicts hyperspectral imaging of human brain tissue samples. Slides containing frozen brain tissue samples from a normal adult human (82 years old) and from an 83 year old patient with AD were obtained. The temporal lobe of the brain was selected for this study due to maximal damage observed in this region due to AD. Spectral signatures were obtained from the cytoplasmic and nuclear regions of normal and AD brain tissues. This demonstrates the applicability of HSI scanning techniques in human tissue samples.
Figure 7:
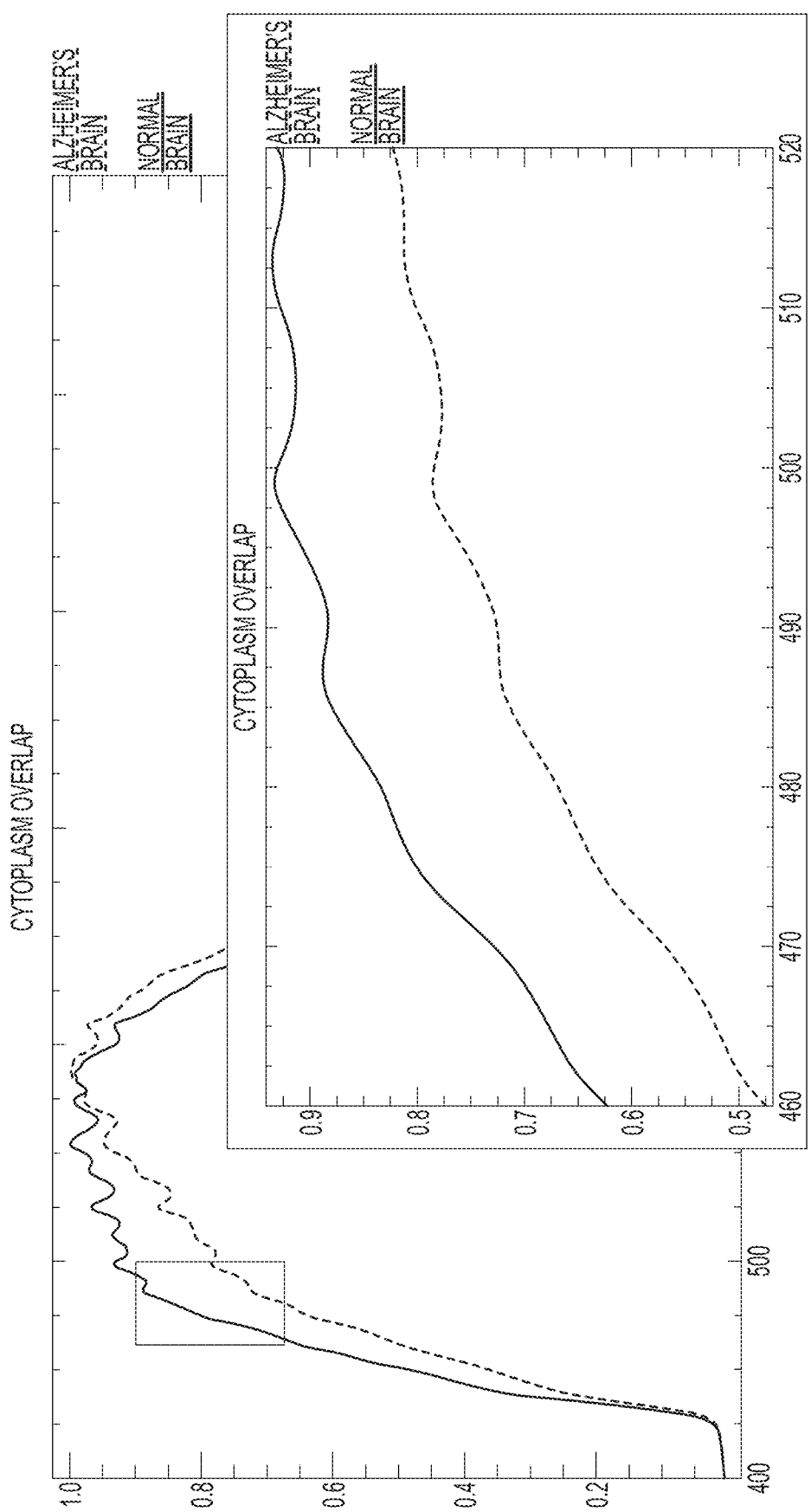
FIG. 7 depicts hyperspectral imaging of human brain tissue samples. This figure shows the spectral changes observed in the brain samples from a normal individual and AD patient. Statistically significant changes were observed in the ranges of (480-500 nm) and (880-1000 nm).
Figure 8:
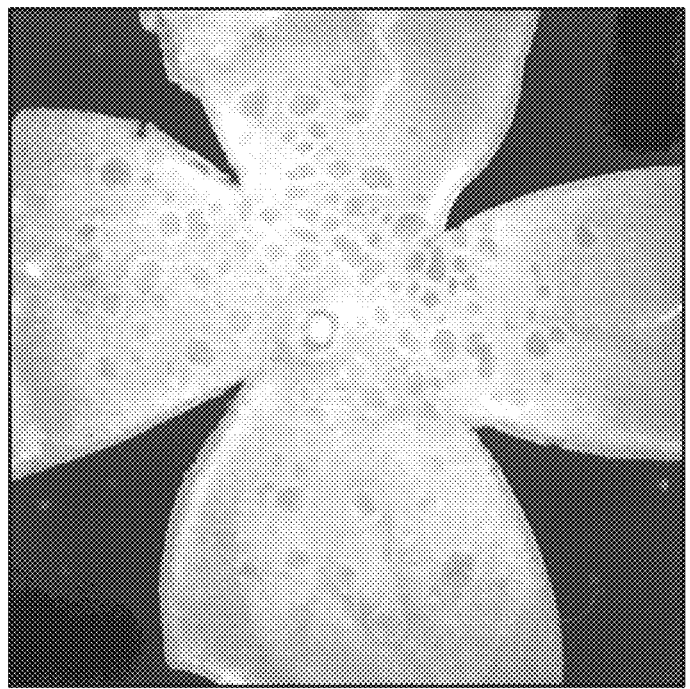
FIG. 8 depicts various parts of an eyeball and an isolated whole mount retina sample.
Figure 8:
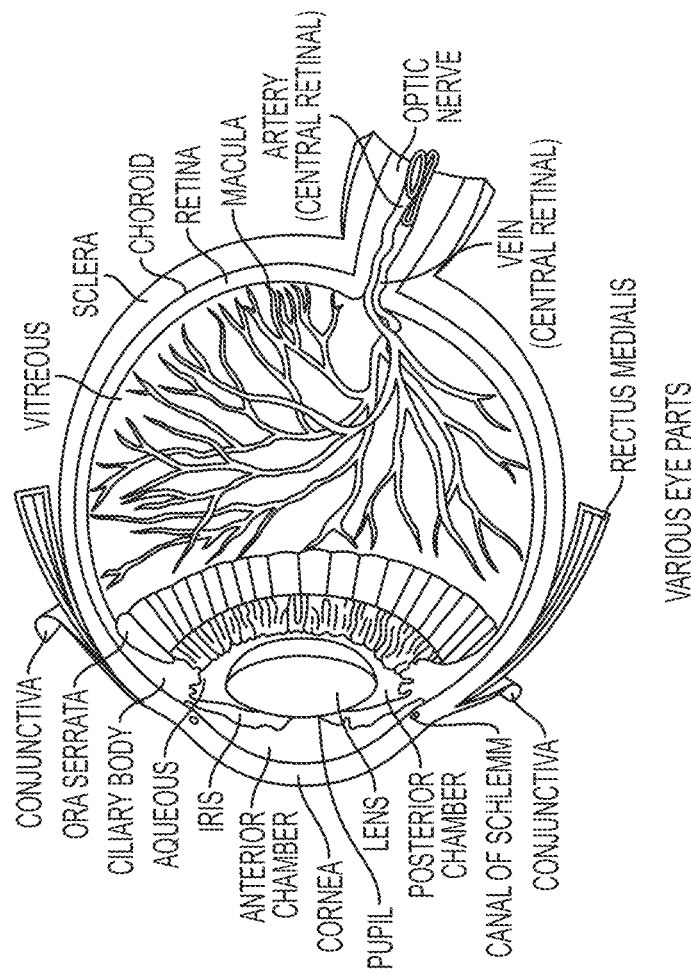
Figure 9:
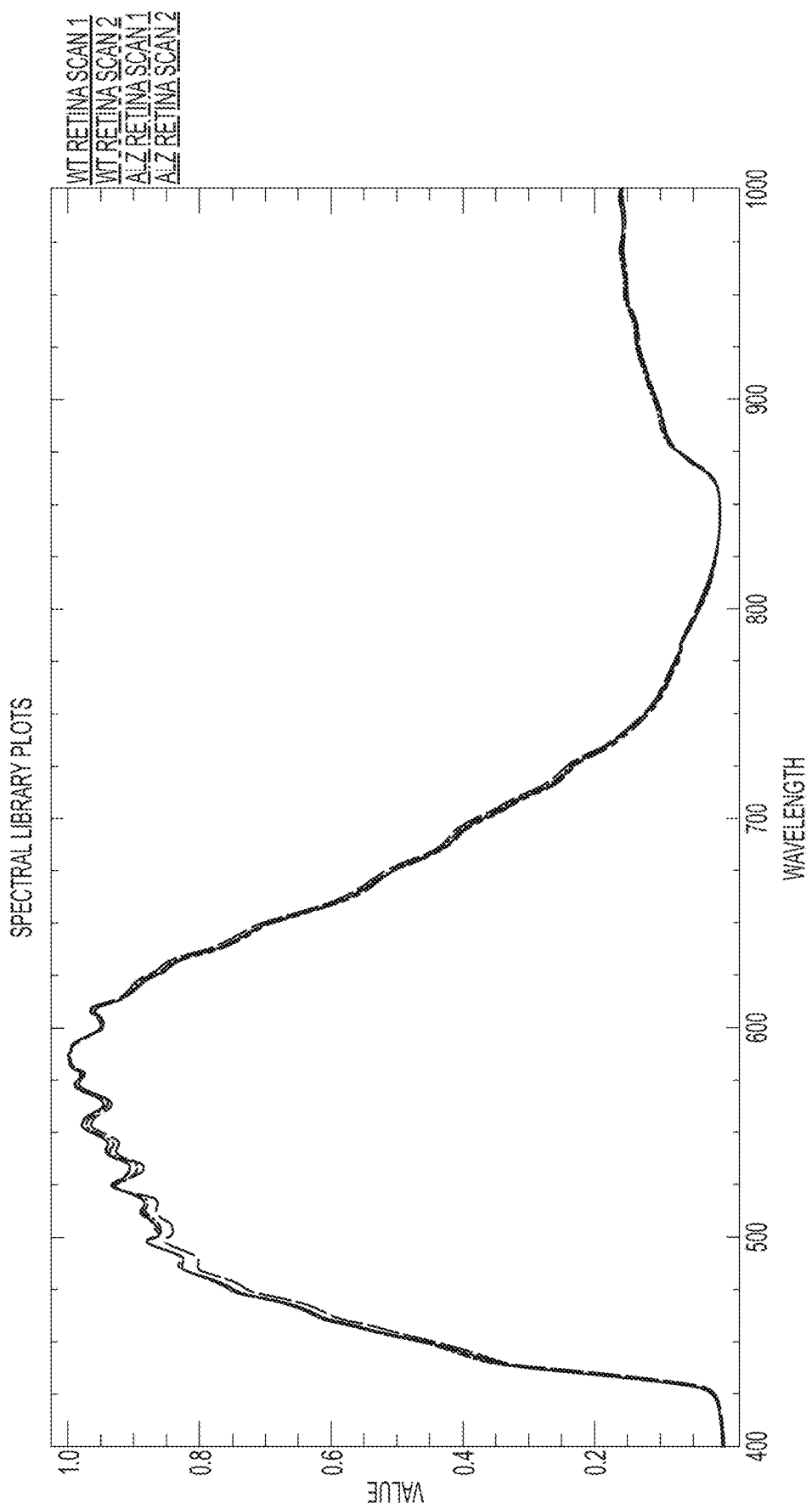
FIG. 9 depicts retina scans of mice at the age of 2 months. Retina tissue was isolated from wild type and transgenic Alzheimer's mice at the age of 2 months. Upon visual inspection, there were no significant differences in the morphology of retina tissue samples obtained from wild type and Alzheimer's mice. The spectral scan showed a trend toward decreased absorbance by Alzheimer's retina as compared to the wild type retina.
Figure 10:
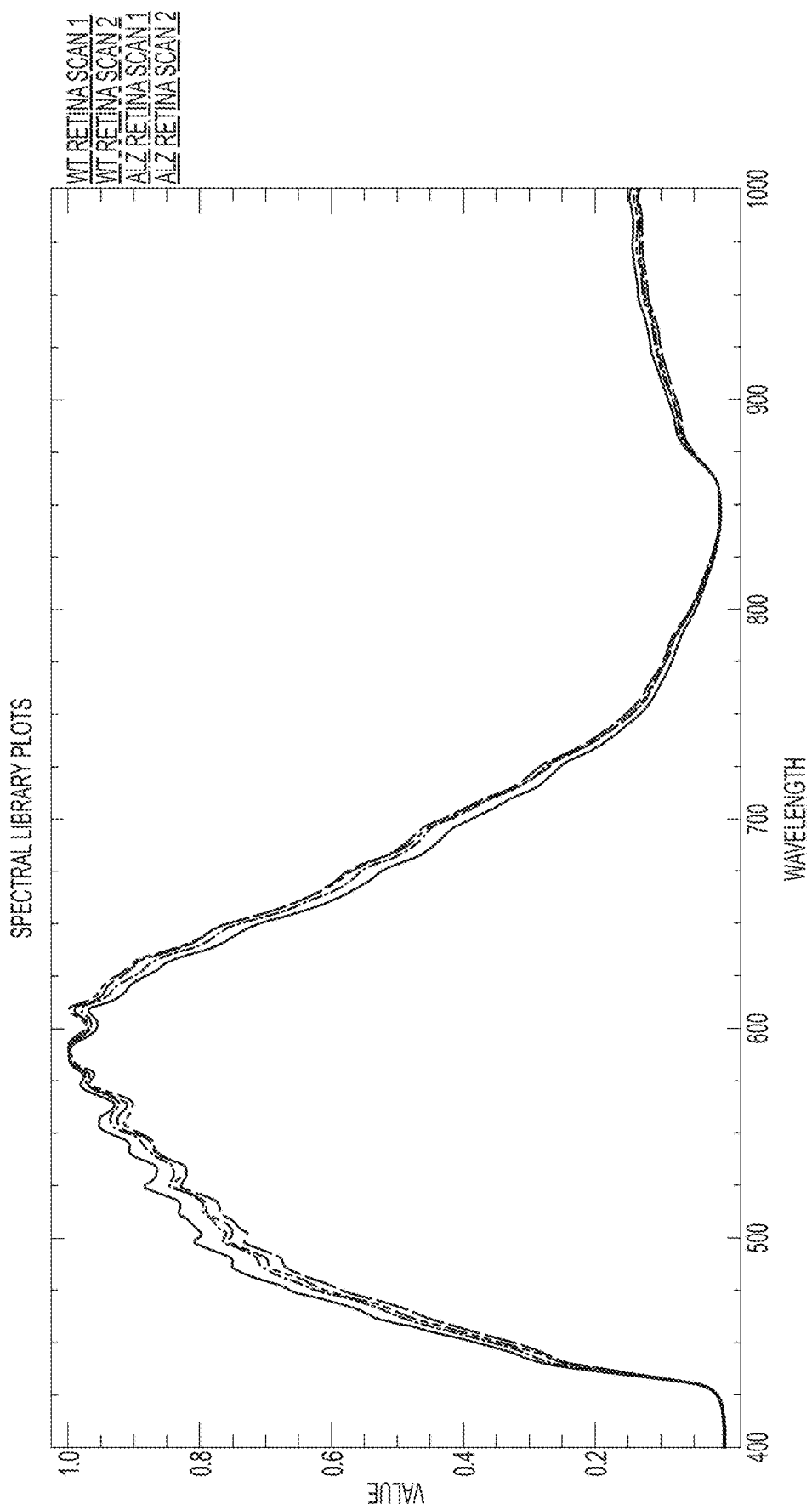
FIG. 10 depicts retina scans of mice at the age of 4 months. Retina tissue was isolated from wild type and transgenic Alzheimer's mice at the age of 4 months. Upon visual inspection, there were no significant differences in the morphology of retina tissue samples obtained from wild type and Alzheimer's mice. The spectral scans of retinas and aqueous eye fluid did not show any significant differences between wild type and Alzheimer's mice.
Figure 11:
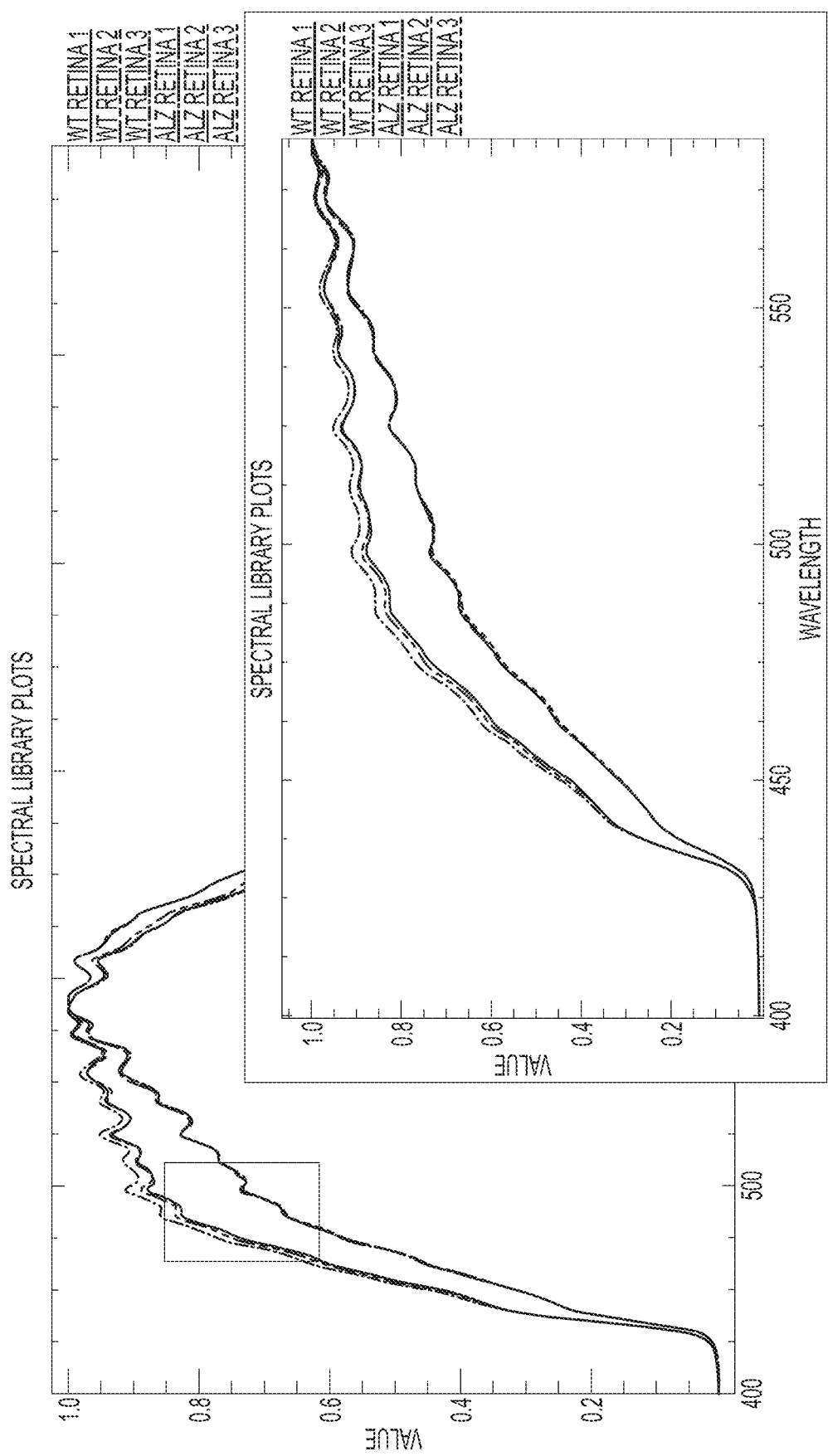
FIG. 11 depicts hyperspectral imaging of mouse retina at 6 months. Upon visual inspection, there were no significant differences in the morphology of retina tissue samples obtained from wild type and Alzheimer's mice at 6 months. However, hyperspectral scans showed significant spectral differences between the wild type (upper 3 traces) and Alzheimer's (lower 2 traces) mice retinae. (At earlier time points (2 and 4 months), there did exist a trend toward a slight difference, but the spectral differences did not reach statistical insignificance.)
Figure 12:
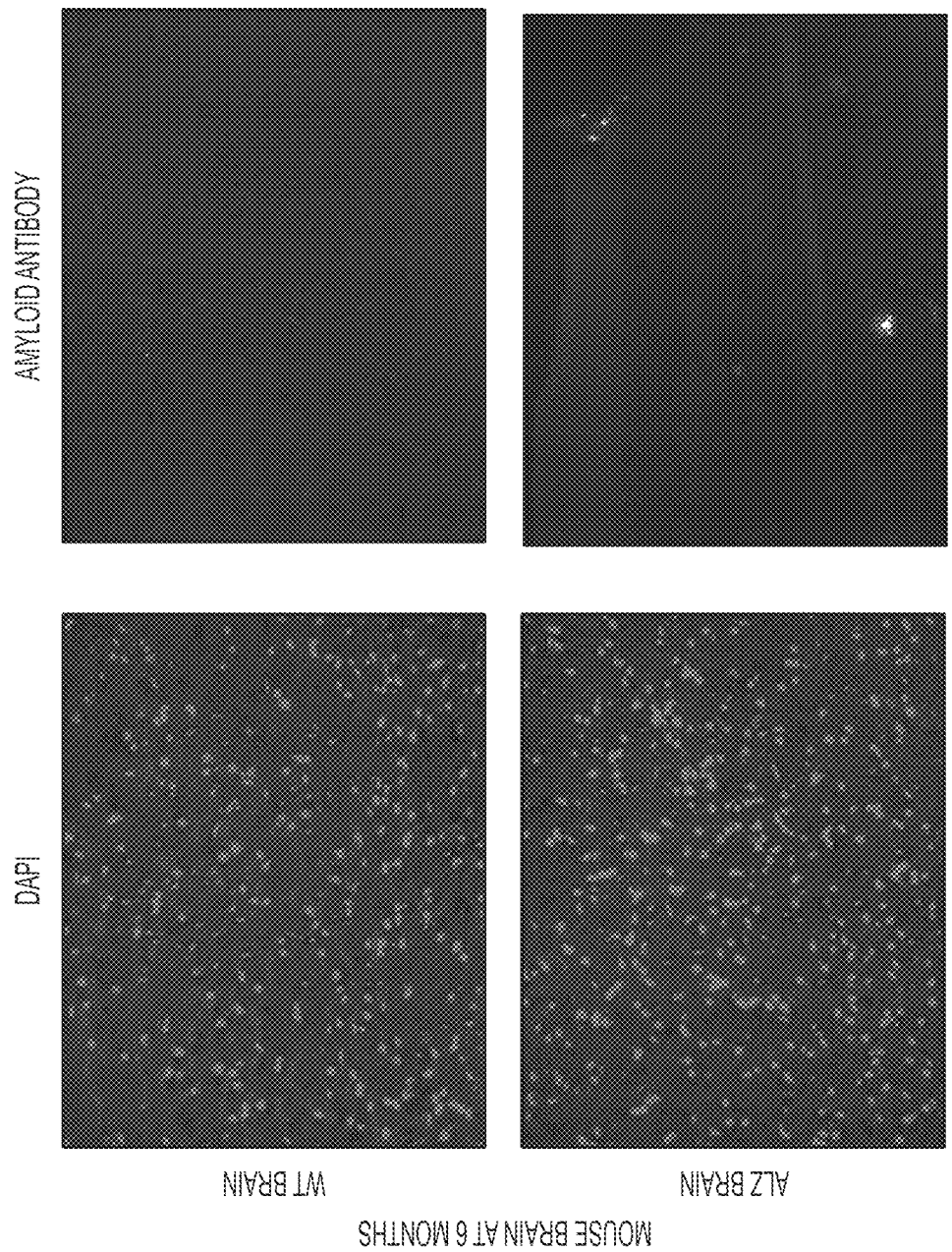
FIG. 12 depicts immunohistochemical staining of mouse brain at 6 months with β-amyloid antibody. This figure shows the staining of mouse brain with β-amyloid antibody at the age of 6 months. The staining in the Alzheimer's brain is not very prominent, however, the spectral changes observed (FIG. 11) in the retina are statistically significant. This shows the early detection capability of HSI.
Figure 13:
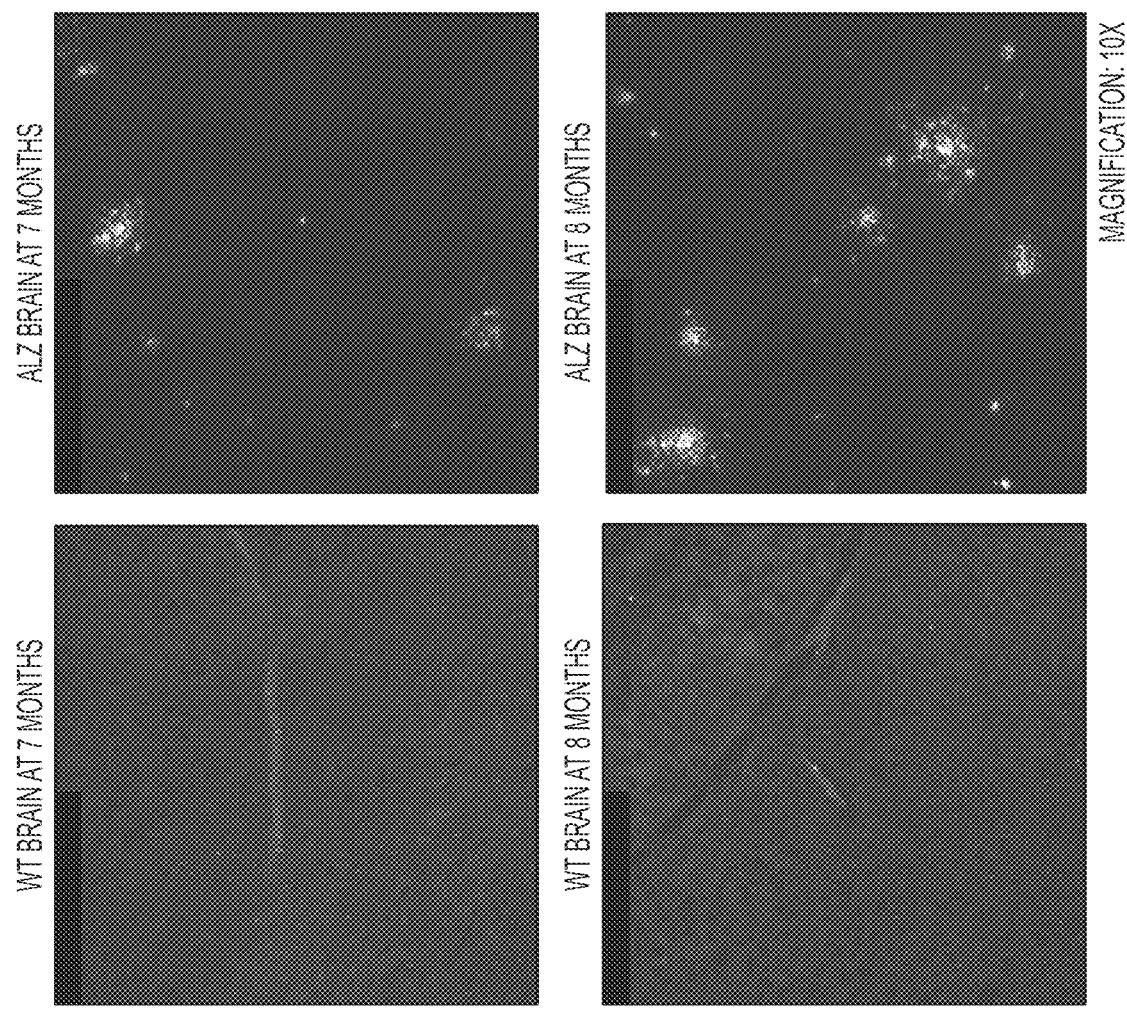
FIG. 13 depicts immunohistochemistry of mouse brain at 7 and 8 months. The number and size of β-amyloid plaques has increased tremendously in the mouse brain at 8 months. The spectral differences in the mouse retina are also showing corresponding increase in the differences between wild type and Alzheimer's mice and are statistically significant.

Described herein is the use of a visible near infrared (VNIR) hyperspectral imaging system as a non-invasive diagnostic tool for early detection of Alzheimer's disease (AD). Also described herein is the use of a VNIR hyperspectral imaging system in high throughput screening of potential therapeutics against AD. In certain aspects, a key principle of this invention is the use of hyperspectral imaging (HSI) as a technique that integrates conventional imaging and spectrophotometry and enables pixel level spectral quantification of the sample being imaged. As an example, the Cytovia-HSI system used captures the VNIR (400-1000 nm) spectrum within each pixel of the scanned field of view with superior signal to noise ratio. By evaluating an expanded spectrum of transmitted light well beyond the visible spectrum, additional information is gained to further characterize the cellular changes caused by β-amyloid aggregation and AD progression.

The utility of HSI spectral analysis in the identification of intracellular amyloid pathology in a variety of test systems was also evaluated. To this end, as described herein, it has been discovered that HSI yields unique and reproducible spectral signatures of amyloid pathology. In every single system tested, including in-vitro cell culture, excised brain tissue and retinal tissue, amyloidogenesis as quantified by HSI correlated well with traditional markers, such as tissue damage and cognitive decline. Such signatures can be extracted from neuronal tissue as well as from retinae. The signatures observed in this study can be obtained well before amyloid-induced morphological and cognitive damage indicators appear. The retinal source of diagnostic HSI data will be very useful for early diagnosis of AD.

As described herein, a HSI system has been developed that can detect cytoplasmic changes before the formation of β-amyloid plaques. Use of several known inhibitors of β-amyloid aggregation can reverse such cytoplasmic changes, demonstrating the usefulness as a high throughput screening method. Furthermore, when applied to the brain from an AD patient, a HSI system detects significant spectral changes that differentiate it from a normal human brain. The advantage of this method over currently known systems is that this method is fast, non-invasive, does not require administration of an external agent and the wavelength region employed is harmless to human tissues. Furthermore, apart from actual brain detection of AD, this technique has been successfully applied to detect the initiation of the disease in the eye (e.g., retinal tissue) well before the development of signs in the brain of a transgenic animal model of AD. This will allow the lead time for treatment of this disease and even effective prophylaxis, which is currently lacking in available detection methods. Certain aspects of the invention are described in relationship to obtaining HSI of the retina. In certain embodiments, other samples such as blood, plasma, urine, spinal fluid or eye fluids besides retinal tissue may be used in the methods described herein.

Certain embodiments of the invention can be used to detect disorders resulting from amyloidopathy and/or amyloidosis, which are pathologies resulting from abnormal protein folding. The final abnormal, and typically toxic, form of the protein is a beta-pleated sheet structure. The primary sequence of the amyloid may vary from disorder to disorder and is not restricted to $A\beta_{1-42}$ (Kyle, British Journal of Haematology (2001), 144(3), 529-538) Examples of such amyloidosis are Alzheimer's disease, cerebral amyloid angiopathy, familial amyloid polyneuropathy, Parkinsons' disease, Huntington's disease and prolactinoma. (see, e.g., Irvine et al., Molecular medicine (Cambridge, Mass.) 14 (7-8): 451-64) Amyloidoses may also include certain infectious diseases such as transmissible spongiform encephalopathies. (e.g., Bovine spongiform encephalopathy or Mad Cow Disease; Nature Structural Biology 8, 281 (2001))

It is noted that wavelengths herein are generally described using the nanometer (nm) description of wavelength. As the art worker appreciates, it is possible to convert these units into another measuring form to describe the wavelengths as an equivalent (e.g., as the wavenumber).

Accordingly, this technology is useful for early detection of Alzheimer's disease in humans via retinal scan as well as the evaluation of the treatment AD patients are exposed to. This method can serve as a tool for high throughput screening of new therapeutics against AD.

While existing technologies provide the detection of AD at very later stages of the disease and thus resulting in the failure of available treatment options, the present invention provides very early detection of the disease. Furthermore this method is non-invasive and does not require administration of external dyes/reagents for detection of β-amyloid plaques.

It has been demonstrated herein that the HSI scanning technique can be employed to screen therapeutics against AD in an in vitro model system. The changes induced by AD in the brain of an AD patient over corresponding normal individual have been successfully detected and confirmed. Furthermore, the HSI scan for early detection of AD using a retinal scan of a transgenic animal model of AD even before any observable changes occur in the brains and retinal tissue of these animals has been successfully employed. Assessment of treatment success of a preclinical drug candidate in a transgenic animal model of AD via retinal HSI spectral analysis and positive correlation of the HSI spectral results with behavioral and biochemical findings has also been demonstrated.

There is major commercial interest in the development of detection systems for neurodegenerative diseases. For AD, there are no available commercial methods that can detect the disease before the onset of any symptoms or before brain-damage. This imaging system is a "first" in this area, in that it provides indications of Alzheimer's disease before onset of brain damage. Furthermore, it is extremely attractive toward commercial development since it does not entail administration of a xenobiotic into the patient. Toxicological testing is not needed because there is no "substance contact" of the imaging system with the patient. The financial barrier here is much, much less than any comparable detection system. Further, there is a need to implement high-throughput screens for potential therapeutics for Alzheimer's disease, but these efforts are hindered by the lack of early-stage detection. Provided herein is a screening system for testing of drugs for early-onset treatment of Alzheimer's disease. Effective, specific "prophylaxis" of Alzheimer's disease has until now been impossible because the early stage of Alzheimer's, when there is no brain damage, has not been detectable with currently available systems. The methods described herein make possible for the first time the design of prophylactics of Alzheimer's disease by providing spectral signature detection of early pathology in the brain and allows for the evaluation of the effectiveness of a treatment.

Evidence suggests that brain damage in AD starts prior to β-amyloid plaque formation. Detection of β-amyloid aggregation at the soluble stage will be helpful for successful treatment. As described herein, it has been demonstrated in in vitro and in vivo model systems that it is possible to detect AD at a very initial stage when there is no detectable damage to the brain. From the drug discovery point of view, currently known screening/testing methods for AD therapeutics rely on dyes (e.g., curcumin, thioflavin-T) for detection of β-amyloid aggregation or employ GFP/FITC tagged β-amyloid peptide in cell based assays. The methods described herein overcome these drawbacks and does not require the addition of an extraneous reagent for inhibitor screening.

The results from HSI based evaluation of the drug treatment can be correlated with other testing methods such as cognition tests, biochemical tests such as degree of oxidative stress, and β-amyloid plaque load in mouse brain. In addition, a 'positive control' for AD treatment can be included based on literature reports, and the results of the positive control can be validated in above said systems. The consensus between the results from HSI analysis and other testing methods will help validate the utility of HSI scanning for determining the degree of success of an AD treatment.

Certain embodiments provide a method for determining whether a subject has Alzheimer's Disease (AD) or is predisposed for developing AD, comprising obtaining a hyperspectral image (HSI) of the retina of the subject over a range of wavelengths to obtain a HSI spectrum and determining whether the spectrum is indicative of the formation of soluble β-amyloid aggregates, wherein the presence of said soluble β-amyloid aggregates indicates the subject has AD or is predisposed for developing AD.

In certain embodiments, the wavelengths used to obtain the HSI spectrum are in the visible near infrared (VNIR) range.

In certain embodiments, the HSI spectrum is compared to at least a first previous HSI spectrum obtained from the subject at an earlier point in time, wherein significant spectral difference between the HSI spectra indicates the subject has AD or is predisposed for developing AD.

In certain embodiments, the HSI from the subject is compared to a control reference HSI spectrum and to an AD reference HSI spectrum to determine whether the image comprises spectral differences that are indicative of AD.

In certain embodiments, the subject is from about 30 to 80 years old (e.g., 30-50 years old).

In certain embodiments, the subject is a male.

In certain embodiments, the subject is a female.

In certain embodiments, the subject is a human.

In certain embodiments, the HSI spectrum is obtained via a retina examination through the whole eye of a patient.

Certain embodiments provide a method for determining whether a treatment is effective in treating or preventing Alzheimer's Disease (AD) or preventing the progress of AD, comprising obtaining a hyperspectral image over range of wavelengths from a retina examination of a subject and determining whether the treatment causes a decrease in formation of soluble β-amyloid aggregates that are indicative of Alzheimer's Disease (AD), wherein a decrease in formation of soluble β-amyloid aggregates is indicative of an effective treatment.

In certain embodiments, the retina examination is a retina examination through the whole eye of a patient.

In certain embodiments, the sample is retinal tissue.

In certain embodiments, the method is an in vitro method.

In certain embodiments, the HSI is a visible near infrared (VNIR) HSI.

Certain embodiments provide a method for using hyperspectral imaging for determining whether a test compound affects β-amyloid aggregation, comprising contacting a cell that comprises β-amyloid with the test compound, obtaining a hyperspectral image (HSI) of the cell over a range of wavelengths to obtain a HSI spectrum, and determining whether HSI spectrum indicates that the test compound affects β-amyloid aggregation.

In certain embodiments, a decrease in β-amyloid aggregation indicates that the test compound is an inhibitor of β-amyloid aggregation.

In certain embodiments, the β-amyloid is $A\beta_{1-42}$.

In certain embodiments, the method is an in vitro method.

In certain embodiments, the method is an in vivo method.

In certain embodiments, the cell is comprised in a population of cells in a retina.

In certain embodiments, the HSI is a visible near infrared (VNIR) HSI.

Certain embodiments provide a method of treatment comprising administering a therapeutic indicated for treatment or prevention of Alzheimer's Disease to a patient from whom a HSI spectrum has been obtained from the patient's retina and wherein the HSI spectrum indicates the patient is presenting with Alzheimer's Disease or is predisposed to developing Alzheimer's Disease.

Certain embodiments provide a method for determining whether a subject has a disorder associated with amyloidopathy and/or amyloidosis or is predisposed for developing a disorder associated with amyloidopathy and/or amyloidosis, comprising obtaining a hyperspectral image (HSI) of the retina of the subject over a range of wavelengths to obtain a HSI spectrum and determining whether the spectrum is indicative of the formation of soluble amyloid aggregates, wherein the presence of said soluble amyloid aggregates indicates the subject has a disorder associated with amyloidopathy and/or amyloidosis or is predisposed for developing a disorder associated with amyloidopathy and/or amyloidosis.

Certain embodiments provide a method for determining whether a treatment is effective in treating or preventing a disorder associated with amyloidopathy and/or amyloidosis or preventing the progress of a disorder associated with amyloidopathy and/or amyloidosis, comprising obtaining a hyperspectral image over range of wavelengths from a retina examination of a subject and determining whether the treatment causes a decrease in formation of soluble amyloid aggregates that are indicative of a disorder associated with amyloidopathy and/or amyloidosis, wherein a decrease in formation of soluble β-amyloid aggregates is indicative of an effective treatment.

Certain embodiments provide a method of treatment comprising administering a therapeutic indicated for treatment or prevention of a disorder associated with amyloidopathy and/or amyloidosis to a patient from whom a HSI spectrum has been obtained from the patient's retina and wherein the HSI spectrum indicates the patient is presenting with a disorder associated with amyloidopathy and/or amyloidosis or is predisposed to developing a disorder associated with amyloidopathy and/or amyloidosis.

In certain embodiments, the disorder associated with amyloidopathy and/or amyloidosis is Alzheimer's disease, cerebral amyloid angiopathy, familial amyloid polyneuropathy, Parkinsons' disease, Huntington's disease, prolactinoma or a transmissible spongiform encephalopathy.

In certain embodiments, the disorder associated with amyloidopathy and/or amyloidosis is bovine spongiform encephalopathy or mad cow disease.

Certain embodiments of the invention will now be illustrated by the following non-limiting Examples.

Example 1 Spectral Scans

CytoViva Hyperspectral Imaging System

After each treatment, slides were examined utilizing a CytoViva microscope and hyperspectral imaging system (CytoViva-Hyperspectral Imaging System (HSI), Auburn, AL) mounted on an Olympus BX-41 optical microscope. This system employs a darkfield-based illuminator that focuses a highly collimated light at oblique angles on the sample to obtain images with improved contrast and signal-to-noise ratio. A concentric imaging spectrophotometer containing aberration-corrected convex holographic diffraction gratings was used with 1.29 nm spectral resolution (12.5 µm slit). The utilization of this concept obviated the necessity of extraneous agents (e.g., staining or contrast agents), as the core imaging technique relies on light scattering/transmittance and resolution of scattered/transmitted light in the visible and near-IR wavelengths. Light scattering is a property unique to every type of insoluble particulate matter, ergo, spectral information relayed by this technique correlates directly to the location and type (or size) of particulate matter in question. In this experiment, the ENvironment for Visualization (ENVI ver. 4.4) software was employed to control the resolution of scattered light and aggregation of β-amyloid peptide was the subject of interest.

The images were captured at 40× magnification using ENVI software, which is followed by extraction of spectral curves as described in the next section. The camera captured spectral responses from 400-1000 nm with a maximum readout time of 12 frames per second. To aid in the identification of $A\beta_{1-42}$ aggregates in unknown samples, a spectral library of $A\beta_{1-42}$ aggregates was created by scanning a stock solution of $A\beta_{1-42}$ peptide which was allowed to oligomerize in vitro. After establishment of this reference library, the spectral angle mapping algorithm was employed for comparison of the distinct spectral features of the library with the spectral scan of the unknown sample (described in Spectral Angle Mapping Classification Algorithm). (see www.cytoviva.com/product_hyperspectral_imaging.htm and Cytoviva Hyperspectral Imaging System Manual)

Acquisition of Spectral Scans from Hyperspectral Image

The CytoViva Hyperspectral image analysis software powered by ENVI contains important features to aid in the quantification and identification of materials by spectral data analysis. At the beginning of each hyperspectral image analysis, images were corrected for dark current values obtained after blocking illumination.

In this system, radiation emanating from cells illuminated with halogen lamp is collected on the objective lens, in turn translating into an image on the entrance-slit plane, which is in turn projected onto the prism-grating-prism components. Consequently, the radiation changes its direction of propagation depending on the wavelength. Each area of the cells is represented as a set of monochromatic points on the detector, translating continually into a spectrum along the spectral axis. Movement of the objective lens amounts to variation in the region captured along with variation the wavelength captured. A set of such images captured at varying camera locations thus yielded all regions and wavelengths of the sample. In these experiments, a total of 3 images were recorded per sample and were analyzed pixel-wise utilizing the Regions of Interest (ROI)® tool. At least ten groups of pixels were analyzed per image. Spectral data was then extracted from each selected ROI and the mean of means of each ROI was calculated based on the following equation:

$$\text{Mean } R(\lambda) = [\text{float}(S1) + (S2) + (S3) + (Sn)] / \text{number of ROIs}$$

Irregularities stemming from non-uniformity of the spectral source and influence of the dark current are accounted for through normalization of the image data. This normalization was performed by considering the highest intensity of a sample in the entire wavelength range i.e. 400-1000 nm as "1" and then calculating the normalized intensity for each wavelength according to the following equation:

$$R(\lambda) = \text{float}(S1)/\max(S1)$$

Each point in the cytoplasm of cells has a sequence of relative transmittance in the entire wavelength range of the spectrum that makes the spectral diagram or spectral signature of a point. In the experiments described herein, the spectral diagrams for cells exposed to desired experimental condition were evaluated to extract the differences between β-amyloid peptide treated and untreated cells in the presence or absence of β-amyloid aggregation promoters or inhibitors. (Siddiqi et al., Cancer. 2008; 114(1):13-21; Khoobehi et al., Invest Ophthalmol Vis Sci. 2004; 45(5):1464-72)

Spectral Angle Mapping Classification Algorithm

Figure 14:
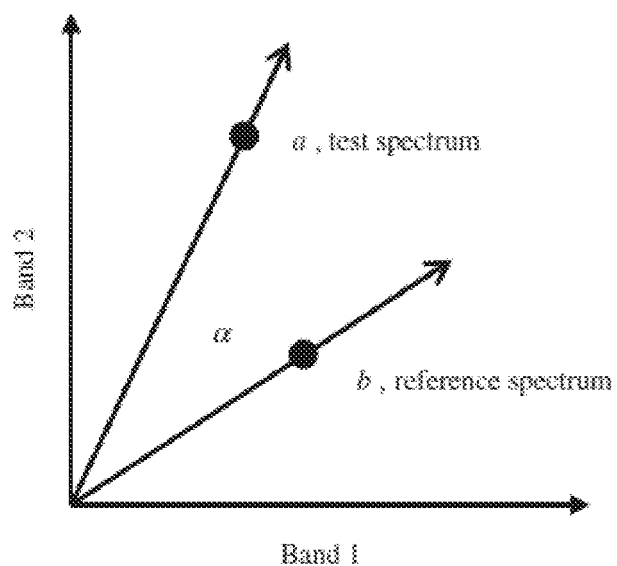
FIG. 14 depicts aspects of a spectral angle mapping (SAM) classification algorithm, which was selected due to its better performance than other classification algorithms for detection of β-amyloid aggregates in unknown samples. (see also Siddiqi et al., Cancer, 114(1), 13-21 (2008)).

Among supervised classification methods, a SAM classification algorithm was selected due to its better performance than other classification algorithms for detection of β-amyloid aggregates in unknown samples. The SAM algorithm is a tool for rapid mapping of the spectral similarity of image spectra to reference spectra. The SAM is a physically based spectral classification that uses an n-dimensional angle to match pixels to reference spectra. This method determines the spectral similarity by calculating the angle between the spectra, treating them as vectors in a space with dimensionality equal to the number of bands or wavelengths. The angle between the endmember spectrum vector and each pixel vector in n-dimensional space is then compared. Smaller angles represent closer match to a reference spectrum. Pixels further away from the specified maximum angle threshold in radians are not classified. In this study, the reference spectra were extracted from region of interest (ROI) in the cytoplasm of cells treated with $A\beta_{1-42}$ peptide. For the SAM classification, the spectral library of $A\beta_{1-42}$ aggregates was created by scanning a stock solution of $A\beta_{1-42}$ peptide which was allowed to oligomerize in vitro and saved in advance. The spectral angle parameter value as α=0·1 or 0·2 was used for a SAM classifier where a is defined as the angle between testing spectrum vector α, and reference spectrum vector b and is calculated using the following equation. (Park et al., Biosys Eng. 2007, 96 (3):323-33)) (Also, see FIG. 14 and Siddiqi et al., *Cancer,* 114(1), 13-21 (2008).

$$\alpha = \cos^{-1}\left(\frac{\vec{a}\cdot\vec{b}}{\|\vec{a}\|\cdot\|\vec{b}\|}\right)$$

Hyperspectral Analysis of Mouse Brain and Retina

Brain and retina tissue were isolated from transgenic Alzheimer's and age-matched wild type mice at 2, 4, 6, 8 and 10 months of age.

(a) Isolation and analysis of brain tissue. Brains were removed from wild type and Alzheimer's mice and post fixed in Zamboni's fixative (4% paraformaldehyde and 15% picric acid in 0.25 M sodium phosphate, pH 7.5) for 48 h before being cryopreserved in a 30% (wt/vol) sucrose/0.1 sodium phosphate-buffered saline solution. Frozen sections (10 μm) in OCT were cut on a sliding microtome, brought to room temperature and were coverslipped with hardset Vectashield mounting medium with the nuclear stain DAPI (catalogue #H-1500; Vector Laboratories, Burlingame, CA). The whole-mount brain slides were scanned with Cytoviva microscope and spectral signatures were collected from wavelengths in the 400-1000 nm range as described before.

(b) Isolation and analysis of retina tissue. Eyes were enucleated from wild type and Alzheimer's mice at the desired age. For whole-mount retinas, eyes were fixed in ~2 mL of freshly prepared 4% PFA-PBS at room temperature for 45 minutes. This was followed by washing with ice-cold PBS solution (2 mL) at least five times. The anterior eye portion, cornea, was dissected out under surgical microscope. The iris was then removed followed by the sclera, lens and hyaloid vessels. The isolated retinas were then washed with ice-cold PBS and divided into four quadrants by making four radial incisions. The whole-mounts were prepared by transferring the dissected retinas onto a microscope slide and coverslipped with hardset Vectashield mounting medium with the nuclear stain DAPI. The whole-mount retina slides were scanned with Cytoviva microscope and spectral signatures were collected from wavelengths in the 400-1000 nm range as described before.

(c) Immunohistochemistry of mouse brain and retina samples. For immunofluorescence studies, brain section slides and retina sample slides were pre-incubated for 1 hour in 5% normal goat serum (NGS) in 1×PBST (1× PBS containing 0.3% Triton X-100) at room temperature. A primary antibody against β-amyloid peptide ((Cell signaling, Cat. #2454) was employed then at a dilution of 1:200 in 1% NGS in 1×PBST. After an overnight incubation at 4° C., the slides were rinsed thrice for 10 min with 1×PBST and then incubated for 2 h in goat anti-rabbit IgG conjugated to Cy3 diluted to 1:1000 in 1% NGS in 1×PBST. The sections were rinsed in PBST thrice for 10 min and in PBS for 5 min. Samples were then dehydrated in ethanol, cleared with methyl salicylate, mounted in DEPEX (Electron Microscopy Science, Poole, UK) and staining of β-amyloid aggregates and plaques was visualized with Cytoviva microscope.

Statistical Analysis of Data

The spectral data were analyzed to detect differences between cells treated with or without β-amyloid peptide in the presence or absence of inhibitors. The differences between the mean transmittance at each wavelength for samples under various treatments were compared by the unpaired Student's t test (two-tailed test) or by the multivariate analysis of variance (ANOVA), as appropriate. Values for each wavelength were reported as means ± SD. A p value of 0.05 was considered significant. Similarly, for tissue samples, spectral differences between Alzheimer's and wild type mouse tissue at a particular time point were analyzed by the unpaired Student's t test with p<0.05 considered to be significant.

Reagents $A\beta_{1-42}$, FITC-$A\beta_{1-42}$ and FITC-scrambled-$A\beta_{1-42}$ were purchased from American Peptide Company (Sunnyvale, CA, USA). All other chemicals were purchased from Sigma (St. Louis, MO, USA). For all experiments, $A\beta_{1-42}$ was dissolved in 1,1,1,3,3,3-hexafluoro-2-propanol (HFIP) to a concentration of 1 mg/mL, sonicated in a water bath for 10 min and dried under vacuum. The HFIP-treated $A\beta_{1-42}$ was dissolved in dimethylsulfoxide (DMSO) to a final concentration of 1 mM and stored at −20° C. Stock solutions of FITC-$A\beta_{1-42}$ and FITC-scrambled-$A\beta_{1-42}$ were prepared in a similar manner. The cell culture media MEM, F12, and fetal bovine serum (FBS) were obtained from Invitrogen (Carlsbad, CA).

Cell Culture and Cellular Uptake.

The human neuroblastoma cell line, SH-SY-5Y, used in the present studies was obtained from American Type Culture Collection (Manassas, VA). The cells were maintained in MEM:F12 (1:1) medium supplemented with 10% FBS, 100 units/mL penicillin and 100 units/mL streptomycin and 1% NEAA (non-essential amino acid). Cells were grown at 37° C. in a humidified atmosphere with 5% CO2/95% air. FITC-A$\beta_{1-42}$, and FITC-scrambled-A$\beta_{1-42}$, were added to SHSY5Y cultures for 24 h. For time-dependence experiments, 250 nM FITC-A$\beta_{1-42}$ was added to SHSY5Y cells, plated in 4-well Lab-Tek chamber slides (Nunc) and images as well as spectral scans (Cytoviva) were acquired at varying times (0-5 days) after addition of the labeled-A$\beta_{1-42}$. For dose-dependence experiments, FITC-A$\beta_{1-42}$ was added at varying concentrations (0-1000 nM) and imaged 24 h thereafter. In some experiments, SH-SY-5Y cells were incubated with FITC-A$\beta_{1-42}$ for 48 h in the presence and absence of inhibitors or promoters of $\beta$-amyloid peptide.

Animals

Female APP and PS1 double transgenic mice (6-8 weeks old, catalogue #005864) and wild type C57BL6 mice were purchased from Jackson Laboratories (Bar Harbor, ME) and housed in SPF conditions, which included filtered air, sterilized food, water, bedding, and cages, for 2 weeks before use. All experiments were approved by the Institutional Animal Care and Use Committee at the University of Minnesota. All experimental and animal handling procedures were in accordance with national ethical guidelines. Mice were maintained on standard food and water ad libitum.

Example 2 Early Detection of Alzheimer's Disease in Humans

Hyperspectral imaging technology can be used for early detection of Alzheimer's disease in humans. To this end, the current Cytoviva® instrument will be modified to enable it to apply light through the retina of the patient and collect the emitted light in such a manner that it can be passed through a Cytoviva spectrophotometer to record spectral data.

The spectral data can in turn be analyzed, e.g., in three ways:
1) As part of an annual exam, a patient may obtain a spectral signature at a particular age and this spectral information will be compared during annual exams in successive years. A significant difference compared to the normal deviation that would occur with age would be considered worthy of further specific evaluation for neurodegenerative disorders.
2) A group of normal and Alzheimer's individuals will be imaged to build a reference spectral library for a particular age range. The spectral data of an unknown individual would be compared to this reference library and its similarity with the two aforementioned groups will be evaluated.
3) Once the person is recognized, either genetically or otherwise through one of the above two novel methods to be susceptible to Alzheimer's disease, treatment may be initiated, with the degree of success of the treatment being tied to deviations from the patient's pre-treatment spectral signature toward the normal group.

In each of the cases, either the entire spectrum in the wavelength range of about 400-1000 nm or only a few selected wavelength ranges can be used for comparison purpose.

Example 3 High Throughput Screening

High throughput screening can be performed in cell culture models as described in Example 2. The changes in hyperspectral scans after the treatment will be compared with the normal and diseased groups. Similarly, the success of AD treatment in humans will be analyzed as described herein.

Example 4 Hyperspectral Imaging: A Tool for Screening of Inhibitors Against $\beta$-Amyloid Aggregation Protein folding constitutes progressive conformational definition of a random coiled polypeptide chain first into finite secondary structures and then into tertiary or quaternary structures that confer functional capability upon the protein. Although regulated strictly by translational order and redox environmental controls, protein folding is not infallible. While a majority of misfolded proteins undergo proteolysis and/or phagocytosis, some resist these so-called "quality control" checks. A small subset of such resistant proteins are toxic on their own accord, and a yet smaller subset are conformational nucleators that induce misfolding in other polypeptide chains. The latter may be exo- or endogenous. Exogenous protein misfolding nucleators are popularly known as prions and prion-induced disease is subject to preventive measures similar to those against DNA-bearing infectious agents. Endogenous protein misfolding nucleators are far more insidious, their origin usually being the misfolding of a normal physiological protein or a polypeptide that is often produced in large quantities. Alzheimer's Disease (AD) molecular pathology showcases a consequence of the misfolding of the amyloid-$\beta$ (A$\beta$) peptide fragments (A$\beta^{1-40}$, A$\beta^{1-42}$), that are produced during proteolysis of the membrane associated amyloid precursor protein. The A$\beta$ peptide fragments are amenable to misfolding into $\beta$-pleated sheet structures that in turn are nucleators of the $\beta$-sheet secondary structure. Higher ordered A$\beta$ sheets are termed fibrils, whose solubility decreases with order. Dense, highly ordered A$\beta$ clumps are the dreaded "plaques" apparent in the post-mortem autopsy of individuals with end-stage AD. Whether A$\beta$ deposition induces cognitive decline or vice-versa is a rather energetically debated matter within the area, nevertheless, there exists agreement that appearance of A$\beta$ plaques is an indicator of AD. Cognitive decline in AD patients was not correlated with the levels of senile plaque formation or insoluble A$\beta$ formation; instead it correlated with the levels of synapse loss and the levels of soluble A$\beta$. These soluble toxic forms of A$\beta$ in AD brains have recently been identified to be oligomeric assemblies of A$\beta$. Thus, amyloid aggregation is thence an attractive therapeutic target for intervention with small molecules.

Amyloidopathy is believed to occur very early in AD development. Early cognitive decline associated with AD (eAD) may be the first clinically tractable pathology, but amyloidopathy is already established firmly at this point. Early intervention into amyloidopathy with small molecules would be fruitful in theory, however, the lack of suitable diagnostic tools for both—the rapid screening of small molecule A$\beta$ aggregation inhibitors and for early detection of AD pathology complicate the drug development and drug administration aspects of AD management. Extant molecular screens for misfolded Aβ are cell-free and consist of dyes (e.g., thioflavin-T, congo red) whose binding to Aβ fibrils causes characteristic spectral change, which is unfortunately subject to variance in the presence of small molecules as would be the case during an inhibitor screen. Mass-spectrometry based screen may be able to identify Aβ fibrillogenesis inhibitors but not those of Aβ oligomerization. Cell-culture and cytotoxicity models thus still remain the mainstay of Aβ aggregation inhibitor screening. All of the existing models of this type employ altered forms of Aβ (such as a GFP-Aβ hybrid) that would aid detection or require unrealistically high concentrations of the expensive Aβ peptide.

Described herein is the development of a detection technique for Aβ aggregation based on the principle of hyperspectral imaging (HSI). A Cytoviva® instrument captures the visible near-IR (400-1000 nm) spectrum within each pixel of the microscopic view field. The information obtained is a spatial distribution of light transmittance with a purportedly high signal-to-noise ratio. In essence, such a high spectral resolution is expected to discern between pixels that represent cytoplasm with varying amounts of unlabelled, native insoluble Aβ, and a wide wavelength range spectral scan beyond the visible range would be expected to highlight characteristic light-transmittance properties of various cytoplasmic components. Described herein are studies examining whether hyperspectral imaging of cytoplasm highlights any characteristic trends that correlate with Aβ accumulation; whether the trend identified is unique to Aβ aggregation, thus paving way for definition of a Aβ accumulation "signature" and hence the foundation of a diagnostic tool, and whether the presence of Aβ aggregation inhibitors is compatible with the collection of hyperspectral images so as to form the basis for a potential high-throughput screen with greatly increased facility and sensitivity when compared to conventional methods.

Results and Discussion.

HSI spectral signature of $A\beta^{1-42}$ aggregation. The uptake of $A\beta^{1-42}$ was verified through incubation of SH-SY5Y cells with 0-1000 nM concentrations of $A\beta^{1-42}$ followed by measurement of intracellular fluorescence. It was demonstrated that cytoplasmic fluorescence intensity rises in proportion to the concentration of $A\beta^{1-42}$ to which the cells are exposed. Organelle distribution of the peptide was not characterized in this experiment, but others have discussed trafficking of $A\beta^{1-42}$ into late lysosomes and vesicles derived therefrom. HSI spectra collected also reveal changes in the 400-1000 nM wavelength region, where transmitted light shifts to lower values, the magnitude of this shift being proportional to the concentration of $A\beta^{1-42}$. The change in light absorbance between the 400-1000 nM wavelength range in the HSI spectra of cells exposed to $A\beta^{1-42}$ appears to be highly specific for the aggregated form of the peptide, as the sequence-scrambled form of $A\beta^{1-42}$, although accumulating to an equal extent inside the cell, does not produce the characteristic HSI shift.

Temporal changes in HSI spectra of cells upon exposure to $A\beta^{1-42}$ were measured by exposure of cells to 250 nM $A\beta^{1-42}$ followed by collection of HSI spectra over time. Transmitted light reduced gradually in the period following 24 h of incubation, reaching its nadir at 48 h. Unexpectedly the period leading up to the 72 h time-point was characterized by gradual regain of light transmittance tending toward values of cells not treated with $A\beta^{1-42}$ or those treated with sequence-scrambled $A\beta^{1-42}$. This trend continued even after week long incubation with the peptide. Macromolecular changes in intracellular amyloid protein content and aggregation and the effects of the changes on spectral characteristics as cells are exposed to beta-amyloid were also determined. Early stages consist of diffusion of amyloid into the cell toward equilibrium with the extracellular space. Continued amyloid accumulation inside the cell results in aggregation. At time=24 h, soluble amyloid fibrils are the dominant amyloid formations and their presence does not alter spectral signature. The period between 24 and 36 h is characterized by amyloid aggregation increasing in order and producing progressively insoluble aggregates that block light and therefore alter spectral signature. Insoluble amyloid aggregates nucleate further ordering of amyloid aggregates into insoluble species resulting in a diffuse mesh of insoluble aggregates at time=48 h. The spectral signature at this time period is correspondingly the most altered when compared to time=0 h. Beyond 48 h, the diffuse mesh of insoluble aggregates begins to coalesce into dense plaques. Although harboring more amyloid content than the diffuse aggregates, the plaques block lesser surface area and the amyloid induced change in spectral signature is apparently reduced.

Utility of the HSI spectral signature in inhibitor screening. Having identified a unique HSI signature for cellular $A\beta^{1-42}$ aggregation, the utility of this finding for screening of inhibitors was investigated. Guanidine, guanosine and urea are known to interfere in amyloid aggregation through sequestration of electrophilic species that form amyloidogenic advanced glycation end-products (AGEs) with proteins. Cells co-incubated with these inhibitors showed attenuation of amyloid-induced HSI spectral change, with some reaching that of cells not treated with $A\beta^{1-42}$. The magnitude of signature-attenuation corresponded to the reported potency of the test inhibitor; thus, guanidine was found to afford the greatest attenuation in HSI spectral change followed sequentially by guanosine and urea—in parallel to their reported potencies of inhibiting amyloid formation inhibition.

HSI spectral signatures in amyloid aggregate mapping and quantitation. The Spectral Angle Mapper (SAM) technique, as described herein, allows obtainment of the spectral signature of a single object—in this case the object being an $A\beta^{1-42}$ aggregate. Utilization of FITC-labelled $A\beta^{1-42}$ enabled visual localization of intracellular aggregates. HSI scanning of the visually located aggregate afforded a specific spectral signature of the aggregate. This process, when repeated across several aggregates revealed that SAM-collected signature of all $A\beta^{1-42}$ aggregates is similar and thus appears to be a unique characteristic. Such a signature can be used for mapping of Aβ aggregates throughout the cytoplasm of an unknown sample. Through this process, the density and the localization of Aβ aggregates could be studied. As a test case, cells were exposed to a known amyloid aggregation inhibitor (guanidine) and a known amyloid aggregation promoter ($Zn^{2+}$). The number of intracellular amyloid aggregates were lowered to 62% in case of cells treated with guanidine when compared to cells treated with $A\beta^{1-42}$ alone. This number changes to 280% in case of $Zn^{2+}$ treated cells. HSI imaging coupled with SAM is thus able to differentiate between amyloid aggregation promoters and inhibitors. This ability to classify compounds according to their amyloidogenic potential will be of interest for drug discovery and toxicology investigations.

Utility of HSI techniques for in-vivo monitoring of amyloidogenesis. HSI spectral signatures from brain samples from patients identified clinically as Alzheimer's inflicted varied from those from age-matched normal individuals.

The type of spectral variation was similar to the characteristic difference observed between normal cells and $A\beta^{1-42}$ treated cells. Total transmittance in the samples from Alzheimer's patients was lower, reflecting dispersion of amyloid aggregates and accompanying morphological and biochemical changes. A similar experiment in retinal tissue samples from normal and Alzheimer's afflicted humans offered similar results.

The retina is considered diagnostically an extension of the CNS and can be accessed with non-invasive methods. The reproducible and tangible differences observed in retinal samples in the present experiments prompted led to the consideration of whether these changes could be used as a potential mode of AD diagnosis.

The retinae of transgenic APP/PS1 mice were imaged with the HSI technique. HSI scans of mice were acquired at 2, 4, 6 and 8 months of age. Differences between normal and APP/PS1 mice began to appear at 4 months of age, and statistically significant differences were observed at the age of 6 months onward. At the age of 6 months, frank amyloid aggregates were not detected in retinal tissue. At the same age, aggregates had begun to appear in the brains of these mice. At the age of 8 months, the HSI spectral difference was prominent and aggregates were clearly observable in brain tissue, but barely visible in the retina. As such, the HSI spectral difference in the retina is independent of the appearance of frank amyloid plaque deposition. Since clinical effects of amyloid plaque deposition appear well after amyloidogenesis has set in, detection of amyloid HSI signature in the retina is an early diagnostic tool for amyloidopathy.

The utility of the HSI imaging diagnostic method in monitoring the development of Alzheimer's disease in a treatment program was evaluated with an experimental anti-Alzheimer's drug candidate, ψ-GSH. (More et al., ACS Chem. Neurosci. 2012, DOI: 10.1021/cn3001679). Transgenic (APP/PS1) and wild type were treated i.p. with ψ-GSH for 12 weeks, beginning at the age of 3 months. Every four weeks, retinae were isolated and HSI spectra were acquired. Retinae at 4 months, i.e., one month after initiation of treatment, showed no statistically significant difference, reciprocating earlier experiments. HSI spectra began to differ between the normal and Alzheimer's mice after 2 months of treatment. The spectra from the retinae of mice treated with W-GSH tended toward those from normal mice. This difference persisted throughout the treatment and 3 months thereafter. Mice treated orally with W-GSH did not exhibit any differences from those of transgenic mice, mirroring the behavioral effects observed in this experiment. These findings were confirmed with the memory test in Morris Water maze and immunohistochemistry on the brain tissue. Mice treated i.p. with ψ-GSH showed significant learned behavior inculcation during the first week of testing, while untreated transgenic mice did not. Escape latencies for mice treated with ψ-GSH (day 3: 17.91±4.65 s; day 4: 14.64±2.61 s) were similar to those for WT saline-treated mice (day 3: 17.29±2.13 s; day 4: 12.42±2.18 s). The escape latency values for the i.p. ψ-GSH treated APP-PS1 mice and those for saline-treated APP-PS1 mice were also significantly different (one-way ANOVA, $p<0.001$). Path lengths traversed by the ψ-GSH treated APP-PS1 mice correlated well with corresponding escape latencies. In fact, ψ-GSH treated APP-PS1 mice traversed paths of lengths similar to saline-treated WT mice. In the probe trial, APP-PS1 mice spent only 16.39±3.39% of the time in the target quadrant, while the APP-PS1 (i.p. ψ-GSH) and non-transgenic vehicle controls retained significantly greater memory, spending 38.43 t 3.73% and 36.67±5.30%, respectively, in the target quadrant. Brain tissue sections of i.p. ψ-GSH treated APP/PS1 mice had significantly lower Aβ load than the corresponding untreated mice. The number and sizes of Aβ plaques were drastically reduced in the ψ-GSH treated group. In APP/PS1 mice treated orally with ψ-GSH, trends toward higher spatial memory development and lower escape latencies were noted relative to the saline-treated group, but did not reach statistical significance. In the probe trial, orally treated APP/PS1 mice spent 21.76±5.36% in the target quadrant; similar to saline treated transgenic controls. Brains of orally treated APP/PS1 mice showed a modest decrease in Aβ plaques relative to controls. Results of biochemical and behavioral studies were in agreement with the hyperspectral data. This provides a basis for utilization of hyperspectral imaging to determine the progress of treatment. This will help avoid lengthy experimentation time and improve the ability to test more compounds.

Materials and Methods

Reagents $A\beta_{1-42}$, FITC-$A\beta_{1-42}$ and FITC-scrambled-$A\beta_{1-42}$ were purchased from American Peptide Company (Sunnyvale, CA, USA). All other chemicals were purchased from Sigma (St. Louis, MO, USA). For all experiments, $A\beta_{1-42}$ was dissolved in 1,1,1,3,3,3-hexafluoro-2-propanol (HFIP) to a concentration of 1 mg/mL, sonicated in a water bath for 10 min and dried under vacuum. The HFIP-treated $A\beta_{1-42}$ was dissolved in dimethylsulfoxide (DMSO) to a final concentration of 1 mM and stored at −20° C. Stock solutions of FITC-$A\beta_{1-42}$ and FITC-scrambled-$A\beta_{1-42}$ were prepared in a similar manner. The cell culture media MEM, F12, and fetal bovine serum (FBS) were obtained from Invitrogen (Carlsbad, CA).

Cell Culture and Cellular Uptake. The human neuroblastoma cell line, SH-SY-5Y, used in the present study was obtained from American Type Culture Collection (Manassas, VA). The cells were maintained in MEM:F12 (1:1) medium supplemented with 10% FBS, 100 units/mL penicillin and 100 units/mL streptomycin and 1% NEAA (non-essential amino acid). Cells were grown at 37° C. in a humidified atmosphere with 5% C02/95% air. FITC-$A\beta_{1-42}$, and FITC-scrambled-$A\beta_{1-42}$, were added to SHSY5Y cultures for 24 h. For time-dependence experiments, 250 nM FITC-$A\beta_{1-42}$ was added to SHSY5Y cells, plated in 4-well Lab-Tek chamber slides (Nunc) and images as well as spectral scans (Cytoviva) were acquired at varying times (0-5 days) after addition of the labeled-$A\beta_{1-42}$. For dose-dependence experiments, FITC-$A\beta_{1-42}$ was added at varying concentrations (0-1000 nM) and imaged 24 h thereafter. In some experiments, SH-SY-5Y cells were incubated with FITC-$A\beta_{1-42}$ for 48 h in the presence and absence of inhibitors or promoters of β-amyloid peptide.

CytoViva hyperspectral imaging System After each treatment, slides were examined utilizing a CytoViva microscope and hyperspectral imaging system (CytoViva-Hyperspectral Imaging System (HSI), Auburn, AL; see the Cytoviva Hyperspectral Imaging System Manual) mounted on an Olympus BX-41 optical microscope. This system employs a darkfield-based illuminator that focuses a highly collimated light at oblique angles on the sample to obtain images with improved contrast and signal-to-noise ratio. Assembly of diffraction grating system in an imaging spectrophotometer with 1.29 nm spectral resolution (12.5 μm slit) was used. Utilization of this concept obviated the necessity of extraneous agents (e.g., staining or contrast agents), as the core imaging technique relies on light scattering/transmittance and resolution of scattered/transmitted light in the visible and near-IR wavelengths. Light scattering is a property unique to every type of insoluble particulate matter, ergo, spectral information relayed by this technique correlates directly to the location and type (or size) of particulate matter in question. In this experiment, the ENvironment for Visualization (ENVI ver. 4.4) software was employed to control the resolution of scattered light and aggregation of β-amyloid peptide was the subject of interest.

The images were captured at 40× magnification using ENVI software, which is followed by extraction of spectral curves as described in the next section. The camera captured spectral responses from 400-1000 nm with a maximum readout time of 12 frames per second. To aid in the identification of $A\beta_{1-42}$ aggregates in unknown samples, a spectral library of $A\beta_{1-42}$ aggregates was created using FITC-labeled $A\beta_{1-42}$ in the cell culture experiments. After establishment of this reference library, the spectral angle mapping algorithm was employed for comparison of the distinct spectral features of the library with the spectral scan of the unknown sample (described in Spectral Angle Mapping Classification Algorithm).

Acquisition of Spectral Scans from Hyperspectral Image The CytoViva Hyperspectral image analysis software powered by ENVI contains features to aid in the quantification and identification of materials by spectral data analysis. At the beginning of each hyperspectral image analysis, images were corrected for dark current values obtained after blocking illumination.

In this system, radiation emanating from cells illuminated with halogen lamp is collected on the objective lens, in turn translating into an image on the entrance-slit plane, which is in turn projected onto the prism-grating-prism components. Consequently, the radiation changes its direction of propagation depending on the wavelength. Each area of the cells is represented as a set of monochromatic points on the detector, translating continually into a spectrum along the spectral axis. Movement of the objective lens amounts to variation in the region captured along with variation the wavelength captured. A set of such images captured at varying camera locations thus yielded all regions and wavelengths of the sample. In these experiments, a total of 3 images were recorded per sample and were analyzed pixel-wise utilizing the Regions of Interest (ROI)® tool. At least ten groups of pixels were analyzed per image. Spectral data was then extracted from each selected ROI and the mean of means of each ROI was calculated based on the following equation:

Mean $R(\lambda)$=[float($S1$)+$S2$+$S3$+ . . . +$Sn$]/number of ROIs

Irregularities stemming from non-uniformity of the spectral source and influence of the dark current are accounted for through normalization of the image data. This normalization was performed by considering the highest intensity of a sample in the entire wavelength range i.e. 400-1000 nm as "1" and then calculating the normalized intensity for each wavelength according to the following equation:

$R(\lambda)$=float($S1$)/max($S1$)

Each point in the cytoplasm of cells has a sequence of relative transmittance in the entire wavelength range of the spectrum that makes the spectral diagram or spectral signature of a point. In these experiments, the spectral diagrams for cells exposed to desired experimental condition were evaluated to extract the differences between β-amyloid peptide treated and untreated cells in the presence or absence of β-amyloid aggregation promoters or inhibitors. (also, see Siddiqi, et al., (2008) Use of hyperspectral imaging to distinguish normal, precancerous, and cancerous cells. Cancer, 114, 13-21 and Khoobehi et al., (2004) Hyperspectral imaging for measurement of oxygen saturation in the optic nerve head. Invest Ophthalmol Vis Sci., 45, 1464-72.)

Spectral Angle Mapping Classification Algorithm Among supervised classification methods, a SAM classification algorithm was selected due to its better performance than other classification algorithms for detection of p-amyloid aggregates in unknown samples. (Park et al., Contaminant Classification of Poultry Hyperspectral Imagery using a Spectral Angle Mapper Algorithm. Biosys Eng., 96, 323-333) The SAM algorithm is a tool for rapid mapping of the spectral similarity of image spectra to reference spectra. The SAM is a physically based spectral classification that uses an n-dimensional angle to match pixels to reference spectra. This method determines the spectral similarity by calculating the angle between the spectra, treating them as vectors in a space with dimensionality equal to the number of bands or wavelengths. The angle between the endmember spectrum vector and each pixel vector in n-dimensional space is then compared. Smaller angles represent closer match to a reference spectrum. Pixels further away from the specified maximum angle threshold in radians are not classified. In this study, the reference spectra were extracted from region of interest (ROI) in the cytoplasm of cells treated with $A\beta_{1-42}$ peptide. For the SAM classification, the spectral library of $A\beta_{1-42}$ aggregates was created by scanning a stock solution of $A\beta_{1-42}$ peptide which was allowed to oligomerize in vitro and saved in advance. The spectral angle parameter value as α=0·1 or 0·2 was used for a SAM classifier where a is defined as the angle between testing spectrum vector a, and reference spectrum vector b and is calculated using the following equation: (Also, see FIG. 14, and Siddiqi et al., Cancer, 114(1), 13-21 (2008).

$$\alpha = \cos^{-1}\left(\frac{\vec{a}\cdot\vec{b}}{\|\vec{a}\|\cdot\|\vec{b}\|}\right)$$

Animals Female APP and PS1 double transgenic mice (6-8 weeks old, catalogue #005864) and wild type C57BL6 mice were purchased from Jackson Laboratories (Bar Harbor, ME) and housed in SPF conditions, which included filtered air, sterilized food, water, bedding, and cages, for 2 weeks before use. All experiments were approved by the Institutional Animal Care and Use Committee at the University of Minnesota. All experimental and animal handling procedures were in accordance with national ethical guidelines. Mice were maintained on standard food and water ad libitum.

Hyeprspectral and Immunohistochemical Analysis of Mouse Brain and Retina Brain and retina tissue were isolated from transgenic Alzheimer's and age-matched wild type mice at 2, 4, 6, and 8 months of age.

(a) Isolation and analysis of brain tissue. Brains were removed from wild type and Alzheimer's mice and post fixed in Zamboni's fixative (4% paraformaldehyde and 15% picric acid in 0.25 M sodium phosphate, pH 7.5) for 48 h before being cryopreserved in a 30% (wt/vol) sucrose/0.1 sodium phosphate-buffered saline solution. Frozen sections (10 μm) in OCT were cut on a sliding microtome, brought to room temperature and were coverslipped with hardset Vectashield mounting medium with the nuclear stain DAPI (catalogue #H-1500; Vector Laboratories, Burlingame, CA). The whole-mount brain slides were scanned with Cytoviva microscope and spectral signatures were collected from wavelengths in the 400-1000 nm range as described.

(b) Isolation and analysis of retina tissue. Eyes were enucleated from wild type and Alzheimer's mice at the desired age. For whole-mount retinas, eyes were fixed in ~2 mL of freshly prepared 4% PFA-PBS at room temperature for 45 minutes. This was followed by washing with ice-cold PBS solution (2 mL) at least five times. The anterior eye portion, cornea, was dissected out under surgical microscope. The iris was then removed followed by the sclera, lens and hyaloid vessels. The isolated retinas were then washed with ice-cold PBS and divided into four quadrants by making four radial incisions. The whole-mounts were prepared by transferring the dissected retinas onto a microscope slide and coverslipped with hardset Vectashield mounting medium with the nuclear stain DAPI. The whole-mount retina slides were scanned with Cytoviva microscope and spectral signatures were collected from wavelengths in the 400-1000 nm range as described before.

(c) Immunohistochemistry of mouse brain and retina samples. For immunofluorescence studies, brain section slides and retina sample slides were pre-incubated for 1 hour in 5% normal goat serum (NGS) in 1× PBST (1× PBS containing 0.3% Triton X-100) at room temperature. A primary antibody against β-amyloid peptide ((Cell signaling, Cat. #2454) was employed then at a dilution of 1:200 in 1% NGS in 1×PBST. After an overnight incubation at 4° C., the slides were rinsed thrice for 10 min with 1×PBST and then incubated for 2 h in goat anti-rabbit IgG conjugated to Cy3 diluted to 1:1000 in 1% NGS in 1×PBST. The sections were rinsed in PBST thrice for 10 min and in PBS for 5 min. Samples were then dehydrated in ethanol, cleared with methyl salicylate, mounted in DEPEX (Electron Microscopy Science, Poole, UK) and staining of β-amyloid aggregates and plaques was visualized with Cytoviva microscope.

Hyperspectral Imaging to follow treatment success in Alzheimer's mice Alzheimer's and wild type mice were treated with a candidate drug, ψ-GSH, three times a week for 12 weeks starting at the age of three to four months. (see More et al., (2012) Restoration of Glyoxalase Enzyme Activity Precludes Cognitive Dysfunction in a Mouse Model of Alzheimer's Disease. ACS Chem. Neurosci., DOI: 10.1021/cn3001679) The study was divided in four groups (10 mice/group). 1. APP/PS1 mice-vehicle control, 2. APP/PS1 mice-ψ-GSH i.p. 500 mg/kg, 3. APP/PS1 mice-W-GSH oral 500 mg/kg, 4. Non-transgenic wild type mice-vehicle control. One and two months after initiation of treatment and at the end of the study, animals were euthanized and retina tissues were isolated from animals in each group followed by hyperspectral imaging as described under "Hyeprspectral Analysis of Mouse Brain and Retina".

Statistical Analysis of data The spectral data were analyzed to detect differences between cells treated with or without β-amyloid peptide in the presence or absence of inhibitors. The differences between the mean transmittance at each wavelength for samples under various treatments were compared by the unpaired Student's t test (two-tailed test) or by the multivariate analysis of variance (ANOVA), as appropriate. Values for each wavelength were reported as means ±SD. Aβ value of 0.05 was considered significant. Similarly, for tissue samples, spectral differences between Alzheimer's and wild type mouse tissue at a particular time point were analyzed by the unpaired Student's t test with $p<0.05$ considered to be significant.

All documents cited herein are incorporated by reference. While certain embodiments of invention are described, and many details have been set forth for purposes of illustration, certain of the details can be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not necessarily impose a limitation on the scope of the invention unless otherwise specifically recited in the claims. No language in the specification should be construed as indicating that any non-claimed element is essential to the practice of the invention.

What is claimed is:

1. A system for spectral imaging, the system comprising:
   a light source for illuminating an eye tissue of a subject over a range of wavelengths;
   one or more detectors for detecting light reflected by the eye tissue; and
   a processor running a software comprising instructions to:
      obtain spectral data of the eye tissue over the range of wavelengths from the light detected by the one or more detectors; and
      analyze the spectral data at multiple light bands over the range of wavelengths to determine whether the spectral data is indicative of at least one of amyloidopathy or amyloidosis in the subject.

2. The system of claim 1, wherein the software is configured to determine whether the spectral data is indicative of a formation of β-amyloid aggregates.

3. The system of claim 2, wherein the β-amyloid aggregates comprise soluble β-amyloid aggregates.

4. The system of claim 2, wherein the β-amyloid aggregates are formed in one or more of a brain, eye, or central nervous system of the subject.

5. The system of claim 1, wherein the range of wavelengths used to obtain the spectral data are in a visible near infrared (VNIR) range.

6. The system of claim 1, wherein the spectral data is hyperspectral data.

7. The system of claim 1, wherein the spectral data is obtained from a hyperspectral image of the eye tissue over the range of wavelengths.

8. The system of claim 1, wherein the software further comprises instructions to compare the spectral data of the eye tissue to at least a first previous spectral data obtained from the eye tissue of the subject at an earlier point in time, wherein significant spectral differences between the spectral data of the eye tissue and the first previous spectral data obtained from the eye tissue indicates the subject has one or more disorders resulting from at least one of amyloidopathy or amyloidosis or is predisposed for developing one or more disorders resulting from at least one of amyloidopathy or amyloidosis.

9. The system of claim 1, wherein the software further comprises instructions to compare the spectral data from the subject to a control spectral data and to a disorder reference spectral data to determine whether the spectral data comprises spectral differences that are indicative of one or more disorders resulting from at least one of amyloidopathy and or amyloidosis.

10. The system of claim 1, wherein the software further comprises instructions to compare the spectral data of the eye tissue to at least a first previous spectral data obtained from the eye tissue of the subject at an earlier point in time, wherein a decrease in formation of soluble β-amyloid aggregates is indicative of an effective treatment of one or more disorders resulting from at least one of amyloidopathy or amyloidosis.

11. The system of claim 1, wherein the spectral data is obtained non-invasively and without administration of dyes for detection of β-amyloid aggregation.

12. The system of claim 1, wherein at least one of amyloidopathy or amyloidosis is indicative of presence or onset of one or more of Alzheimer's disease, cerebral amyloid angiopathy, familial amyloid polyneuropathy, Parkinsons' disease, Huntington's disease, prolactinoma or a transmissible spongiform encephalopathy.

13. The system of claim 1, wherein the light source is a halogen light source.

14. The system of claim 1, further comprising an objective lens configured to collect light reflected by the eye tissue.

15. The system of claim 1, further comprising a dispersive element.

16. The system of claim 15, wherein the dispersive element comprises a prism.

17. A system for spectral imaging, the system comprising:
a light source for illuminating an eye tissue of a subject over a range of wavelengths;
one or more detectors for detecting light reflected by the eye tissue; and
a processor running a software comprising instructions to:
obtain spectral data of the eye tissue over the range of wavelengths from the light detected by the one or more detectors; and
analyze the spectral data at multiple light bands over the range of wavelengths to determine whether the spectral data is indicative of a formation of amyloid aggregates.

18. The system of claim 17, wherein the range of wavelengths used to obtain the spectral data are in a visible near infrared (VNIR) range.

19. The system of claim 17, wherein the spectral data is hyperspectral data.

20. The system of claim 17, wherein the spectral data is obtained from a hyperspectral image of the eye tissue over the range of wavelengths.

21. The system of claim 17, wherein the amyloid aggregates are indicative of a disorder or a predisposition associated with at least one of amyloidopathy or amyloidosis in the subject, wherein the disorder is cerebral amyloid angiopathy, familial amyloid polyneuropathy, Alzheimer's disease, Parkinson's disease (PD), Huntington's disease, prolactinoma or a transmissible spongiform encephalopathy.

22. The system of claim 21, wherein the software further comprises instructions to compare the spectral data of the eye tissue to at least a first previous spectral data obtained from the eye tissue of the subject at an earlier point in time, wherein significant spectral difference between the spectral data of the eye tissue and the first previous spectral data obtained from the eye tissue indicates the subject has PD or is predisposed for developing PD.

23. The system of claim 21, wherein the software further comprises instructions to compare the spectral data from the subject to a control spectral data and to a PD reference spectral data to determine whether the spectral data comprises spectral differences that are indicative of PD.

24. The system of claim 21, wherein the software further comprises instructions to compare the spectral data of the eye tissue to at least a first previous spectral data obtained from the eye tissue of the subject at an earlier point in time, wherein a decrease in information of soluble β-amyloid aggregates is indicative of an effective treatment of PD.

25. A system for spectral imaging, the system comprising:
a light source for illuminating a cell over a range of wavelengths;
one or more detectors for detecting light reflected by the cell; and
a processor running a software comprising instructions to:
obtain spectral data of the cell over the range of wavelengths from the light detected by the one or more detectors; and
analyze the spectral data at multiple light bands over the range of wavelengths to determine whether the spectral data is indicative of a progression of one or more disorders associated with at least one of amyloidopathy or amyloidosis.

26. The system of claim 25, wherein the one or more disorders comprise cerebral amyloid angiopathy, familial amyloid polyneuropathy, Alzheimer's disease, Parkinson's disease (PD), Huntington's disease, prolactinoma or a transmissible spongiform encephalopathy.

* * * * *

UNITED STATES PATENT AND TRADEMARK OFFICE
CERTIFICATE OF CORRECTION

| | |
|---|---|
| PATENT NO. | : 11,819,276 B2 |
| APPLICATION NO. | : 17/939566 |
| DATED | : November 21, 2023 |
| INVENTOR(S) | : Robert Vince and Swati Sudhakar More |

It is certified that error appears in the above-identified patent and that said Letters Patent is hereby corrected as shown below:

In the Claims

Column 21, Lines 10-11, Claim 9, delete "amyloidopathy and or amyloidosis" and insert -- amyloidopathy or amyloidosis --; and Column 22, Line 30, Claim 24, delete "decrease in information of" and insert -- decrease in formation of" -- therefor.

Signed and Sealed this
Twentieth Day of February, 2024

Katherine Kelly Vidal
*Director of the United States Patent and Trademark Office*